US012788982B2

(12) United States Patent
Noble et al.

(10) Patent No.: US 12,788,982 B2
(45) Date of Patent: Nov. 10, 2026

(54) GRAPH-BASED METHOD FOR OPTIMAL ACTIVE ELECTRODE SELECTION IN COCHLEAR IMPLANTS AND APPLICATIONS OF SAME

(71) Applicant: VANDERBILT UNIVERSITY, Nashville, TN (US)

(72) Inventors: Jack H. Noble, Nashville, TN (US); Erin Bratu, Nashville, TN (US); Benoit M. Dawant, Nashville, TN (US); Robert F. Labadie, Nashville, TN (US); Rene H. Gifford, Franklin, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 841 days.

(21) Appl. No.: 17/948,737

(22) Filed: Sep. 20, 2022

(65) Prior Publication Data

US 2023/0104152 A1 Apr. 6, 2023

Related U.S. Application Data

(60) Provisional application No. 63/246,501, filed on Sep. 21, 2021.

(51) Int. Cl.
*A61N 1/36* (2006.01)

(52) U.S. Cl.
CPC ................................ *A61N 1/36038* (2017.08)

(58) Field of Classification Search
CPC .................................................. A61N 1/36038
See application file for complete search history.

(56) References Cited

PUBLICATIONS

Zhao Y, Dawant BM, Noble JH. Automatic selection of the active electrode set for image-guided cochlear implant programming. J Med Imaging (Bellingham). Jul. 2016;3(3):035001. doi: 10.1117/1.JMI.3.3.035001. Epub Sep. 22, 2016. PMID: 27704031; PMCID: PMC5031788. (Year: 2016).*

Noble JH, Dawant BM. Automatic graph-based localization of cochlear implant electrodes in CT. Med Image Comput Comput Assist Interv. Oct. 2015;9350:152-159. doi: 10.1007/978-3-319-24571-3_19. Epub Nov. 20, 2015. PMID: 27158686; PMCID: PMC4854292. (Year: 2015).*

NIDCD Quick Statistics About Hearing, https://www.nidcd.nih.gov/health/statistics/quick-statistics-hearing, last accessed Mar. 13, 2020.

(Continued)

*Primary Examiner* — Allen Porter
*Assistant Examiner* — Shreya Anjaria
(74) *Attorney, Agent, or Firm* — troutman pepper locke; Tim Tingkang Xia, Esq.

(57) ABSTRACT

A method for active electrode selection in a cochlear implant having an electrode array with a plurality of electrodes implanted in a cochlea of a living subject. The method includes estimating an activation region (AR) of each electrode based on its distance to nerve sites; presenting the AR in a visualization representation, wherein each electrode is represented by a bar having a width or length representing the AR; identifying electrodes having substantial AR overlap if the AR of one electrode overlaps substantially with the AR bar of another electrode; and selecting and deactivating at least one of the identified electrodes with substantial AR overlap.

11 Claims, 11 Drawing Sheets
(11 of 11 Drawing Sheet(s) Filed in Color)

(56) References Cited

PUBLICATIONS

NIDCD Fact Sheet: Cochlear Implants. National Institute on Deafness and Other Communication Disorders. NIH Publication No. 11-4798. https://www.nidcd.nih.gov/sites/de- fault/files/Documents/health/hearing/FactSheetCochlearImplant.pdf, last accessed Mar. 12, 2020.
Holden, L., Finley, C., Firszt, J., et al.: Factors affecting open-set word recognition in adults with cochlear implants. Ear Hear 34, 342-360 (2013).
Finley, C., Skinner, M.: Role of electrode placement as a contributor to variability in cochlear implant outcomes. Otol Neurotol 29, 920-928 (2008).
Chakravorti, S., Noble, J., Gifford, R., Dawant, B., O'Connell, B., Wang, J., Labadie, R.: Further evidence of the relationship between cochlear implant electrode positioning and hearing outcomes. Otology & Neurotology 40(5), 617-624 (2019).
Aschendorff, A., et al: Quality control after cochlear implant surgery by means of rotational tomography. Otology & Neurotology 26(1), 34-37 (2005).
Wanna, G., et al: Impact of electrode design and surgical approach on scalar location and cochlear implant outcomes. Laryngoscope 124(6), S1-S7 (2014).
Wanna, G., et al: Assessment of electrode placement and audiologic outcomes in bilateral cochlear implantation. Otology & Neurotology 32(3), 428-432 (2011).
O'Connell B.P., et al: Electrode location and angular insertion depth are predictors of audi-ologic outcomes in cochlear implantation. Otology & Neurotology 37(8), 1016-1023 (2016).
Noble, J.H., Labadie, R.F., Gifford, R.H., and Dawant, B.M.: Image-guidance enables new methods for customizing cochlear implant stimulation strategies. IEEE Trans. on Neur. Sys. and Rehab. Eng. 21(5), 820-829 (2013).
Noble, J.H., Gifford, R.H., Labadie, R.F., and Dawant, B.M.: Statistical shape model segmentation and frequency mapping of cochlear implant stimulation targets in CT. Proc. MICCAI 2012 LNCS vol. 15(2), 421-428 (2012).
Zhao, Y., et al.: Automatic graph-based method for localization of cochlear implant electrode arrays in clinical CT with sub-voxel accuracy. Med. Image Anal. 52, 1-12 (2019).
Noble, J.H., Dawant, B.M.: Automatic graph-based localization of cochlear implant electrodes in CT. In: Navab, N., Hornegger, J., Wells, W.M., Frangi, A.F. (eds.) MICCAI 2015. LNCS, vol. 9350, pp. 152-159. Springer, Cham (2015). https://doi.org/10.1007/978-3-319-24571-3_19.
Baer, T. and Moore, B.C.J.: Effects of spectral smearing on the intelligibility of sentences in the presence of interfering speech. J. Acoust. Soc. Am. 95, 2277-2280 (1994).
Kwon, B.J.: Effects of electrode separation between speech and noise signals on consonant identification in cochlear implants. J. Acoust. Soc. Am. 126(6): 3258-67 (2009). https://doi.org/10.1121/1.3257200.
Berg, K.A., Noble, J.H., Dawant, B.M., Dwyer, R.T., Labadie, R.F., Gifford, R.H.: Speech recognition as a function of the number of channels for an array with large inter-electrode distances. J. Acoust. Soc. Am. 149 (4): 2752-63 (2021).
Rattay, F., Leao, R.N., and Felix, H.: A model of the electrically excited human cochlear neuron. II. Influence of the three-dimensional cochlear structure on neural excitability. Hear Res 153(1-2), 64-79 (2001).
Ceresa, M., Lopez, N.M., Velardo, H.D., Herrezuelo, N.C., Mistrik, P., Kjer, H.M., Vera, S., Paulsen, R.R., and Ballester, M.A.G.: Patient-specific simulation of implant placement and function for cochlear implantation surgery planning. Proc. MICCAI 2014 LNCS vol. 8674, 49-56 (2014).
Zhao, Y., Dawant, B.M., and Noble, J.H.: Automatic selection of the active electrode set for image-guided cochlear implant programming. Journal of Medical Imaging vol. 3(3), 035001 (2016).
Bratu, E.L., Dwyer, R., and Noble, J.H.: A graph-based method for optimal active electrode selection in cochlear implants. Proc. MICCAI 2020 LNCS vol. 12263, 34-43 (2020).
Zhang, D., Zhao, Y., Noble, J.H., Dawant, B.M: Selecting electrode configurations for image-guided cochlear implant programming using template matching. Journal of Medical Imaging, vol. 5(2), 021202 (2018).

* cited by examiner

GRAPH-BASED METHOD FOR OPTIMAL ACTIVE ELECTRODE SELECTION IN COCHLEAR IMPLANTS AND APPLICATIONS OF SAME

CROSS-REFERENCE TO RELATED PATENT APPLICATION

This application claims priority to and the benefit of U.S. Provisional Patent Application Ser. No. 63/246,501, filed Sep. 21, 2021, which is incorporated herein in its entirety by reference.

STATEMENT AS TO RIGHTS UNDER FEDERALLY-SPONSORED RESEARCH

This invention was made with government support under Grant Nos. DC014037, and DC014462, awarded by the National Institutes of Health. The government has certain rights in the invention.

FIELD OF THE INVENTION

The invention relates generally to cochlear implants, and more particularly, to graph-based method for optimal active electrode selection in cochlear implants and applications of the same.

BACKGROUND OF THE INVENTION

The background description provided herein is for the purpose of generally presenting the context of the invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions. Work of the presently named inventors, to the extent it is described in the background of the invention section, as well as aspects of the description that may not otherwise qualify as prior art at the time of filing, are neither expressly nor impliedly admitted as prior art against the invention.

Over the last three decades, the cochlear implant (CI) has become the standard-of-care for severe-to-profound sensorineural hearing loss (SNHL), with an estimated 736,900 devices implanted worldwide as of 2019, including approximately 118,100 and 65,000 in American adults and children, respectively. SNHL is characterized by insufficient stimulation of the auditory nerve fibers (ANFs) composing the cochlear neuron housed within the modiolus (shown in green in FIG. 1A) to produce the typical range of human hearing. To counter this, the CI bypasses the mechanisms of acoustic hearing, in which vibrations from sounds reaching the cochlea stimulate hair cells that activate ANFs to produce the sensation of sound, by directly stimulating the ANFs using an electrode array surgically inserted into the cochlea. This array is connected to other internal protective circuitry and a receiver/stimulator with an RF coil placed between the scalp and skull, which is then magnetically connected to a removable processor worn on the exterior of the scalp. Sounds detected by a microphone in the processor are decomposed into their frequency components, which the processor uses to determine how power distributed to the electrodes of the array according to a set of processor instructions, also referred to as a patient's map. An audiologist can customize this map to improve a patient's hearing outcomes by modifying the set of activated electrodes, the dynamic range of each electrode, and the frequency range assigned to each electrode.

The differences in neural activation in acoustic versus electrically-induced hearing can pose significant challenges for programming CIs. The auditory nerve is composed of approximately 30,000 ANFs, each of which has an associated characteristic frequency. The ANF is activated by hair cell stimulation only when the acoustic signal contains energy at the highly selective characteristic frequency associated with the ANF. These ANFs are arranged tonotopically along the length of the cochlea, meaning different regions of the cochlea are associated with different frequencies of sound. The typical range of human hearing falls between 20 Hz and 20 kHz, with the highest characteristic frequencies associated with ANFs at the entrance, or basal end, of the cochlea and the lowest associated with the deepest, or most apical, nerve sites, as shown in FIG. 1A. However, CIs provide far fewer unique frequency channels, with implants from the three FDA-approved CI manufacturers only having between 12 and 22 electrodes from which audiologists must reconstruct the range of human hearing. Because of this, a single ANF will be stimulated for more frequencies than just its characteristic frequency and also may receive stimulation from multiple electrodes, further increasing the frequency range for which it will be stimulated. This overlapping stimulation, also referred to as channel interaction, can create spectral smearing artifacts that reduce hearing outcomes.

Therefore, a heretofore unaddressed need exists in the art to address the aforementioned deficiencies and inadequacies.

SUMMARY OF THE INVENTION

In one aspect, the invention relates to a method for active electrode selection in a cochlear implant having an electrode array with a plurality of electrodes implanted in a cochlea of a living subject. The method includes estimating an activation region (AR) of each electrode based on its distance to nerve sites; presenting the AR in a visualization representation, wherein each electrode is represented by a bar having a width or length representing the AR; identifying electrodes having substantial AR overlap if the AR of one electrode overlaps substantially with the AR bar of another electrode; and selecting and deactivating at least one of the identified electrodes with substantial AR overlap.

In one embodiment, the AR of the electrode is a group of nerve sites that satisfy $$R = \frac{|E(\vec{x})|}{|E(PAR)|} = \frac{\|PAR - \vec{c}\|^2}{\|\vec{x} - \vec{c}\|^2} > \tau$$

wherein $|E(\vec{x})|$ and $|E(PAR)|$ are electric field strengths from the electrode $\vec{c}$ at a nerve site $\vec{x}$ of the group of nerve sites and the PAR, respectively, R is a ratio of the electric field strength from the electrode at the nerve site to that at the PAR, and $\tau$ is a threshold value used to determine the AR for each electrode.

In one embodiment, the threshold value τ defines a tolerance for the activation region overlapping between electrodes, and large values for the threshold value τ indicate a greater tolerance for the activation region overlapping between the electrodes, producing a narrower AR, while small values for the threshold value τ indicate less tolerance for the activation region overlapping between the electrodes, resulting in a larger AR.

In one embodiment, τ=0.5.

In one embodiment, the visualization representation has a horizontal axis representing characteristic frequencies (CF) of the spiral ganglion, and a vertical axis representing each electrode of the electrode array, with each horizontal colored bar associated with one electrode.

In one embodiment, the most apical electrode is located at the bottom of the visualization representation, and the most basal electrode is located at the top of the visualization representation.

In one embodiment, said selecting and deactivating step further comprises deactivating any electrode with a PAR with characteristic frequency greater than 15 kHz.

In one embodiment, the graph-based method further includes coding operation states of each electrode with different colors in the visualization representation, comprising coding the electrode with a first color if it is activated and does not have significant interaction with another electrode; a second color if it is deactivated; a third color if it is activated but has significant interaction with another electrode; or a fourth color if it is deactivated but could be activated without having significant interaction with another electrode.

In one embodiment, the visualization representation comprises a graphical user interface (GUI), configured such that changing any of available options in the GUI automatically triggers the visualization representation to reassess constraint violations and update the color for each electrode accordingly.

In another aspect, the invention relates to a method for automatically selecting electrodes to deactivate for image guided cochlear implant programming (IGCIP), comprising configuring the plurality of electrodes of the electrode array implanted in the cochlea of the living subject using the above disclosed method.

In yet another aspect, the invention relates to a system for optimal active electrode selection and deactivation. The system comprises a CI device being implanted in a cochlea of a living subject, the CI device comprising an electrode array having a plurality of electrodes; and at least one computing device having one or more processors and a storage device storing computer executable code, wherein the computer executable code, when executed at the one or more processors, is configured to perform functions for active electrode selection. The functions includes estimating an AR of each electrode based on its distance to nerve sites; presenting the AR in a visualization representation, wherein each electrode is represented by a bar having a width or length representing the AR; identifying electrodes having substantial AR overlap if the AR of one electrode overlaps substantially with the AR bar of another electrode; and selecting and deactivating at least one of the identified electrodes with substantial AR overlap.

In one embodiment, the AR of the electrode is a group of nerve sites that satisfy $$R = \frac{|E(\vec{x})|}{|E(PAR)|} = \frac{\|PAR - \vec{c}\|^2}{\|\vec{x} - \vec{c}\|^2} > \tau$$

wherein $|E(\vec{x})|$ and $|E(PAR)|$ are electric field strengths from the electrode $\vec{c}$ at a nerve site $\vec{x}$ of the group of nerve sites and the PAR, respectively, R is a ratio of the electric field strength from the electrode at the nerve site to that at the PAR, and τ is a threshold value used to determine the AR for each electrode.

In one embodiment, the threshold value τ defines a tolerance for the activation region overlapping between electrodes, and large values for the threshold value τ indicate a greater tolerance for the activation region overlapping between the electrodes, producing a narrower AR, while small values for the threshold value τ indicate less tolerance for the activation region overlapping between the electrodes, resulting in a larger AR.

In one embodiment, τ=0.5.

In one embodiment, the visualization representation has a horizontal axis representing CF of the spiral ganglion, and a vertical axis representing each electrode of the electrode array, with each horizontal colored bar associated with one electrode.

In one embodiment, the most apical electrode is located at the bottom of the visualization representation, and the most basal electrode is located at the top of the visualization representation.

In one embodiment, said selecting and deactivating step further comprises deactivating any electrode with a PAR with characteristic frequency greater than 15 kHz.

In one embodiment, the graph-based method further includes coding operation states of each electrode with different colors in the visualization representation, comprising coding the electrode with a first color if it is activated and does not have significant interaction with another electrode; a second color if it is deactivated; a third color if it is activated but has significant interaction with another electrode; or a fourth color if it is deactivated but could be activated without having significant interaction with another electrode.

In one embodiment, the visualization representation comprises a GUI, configured such that changing any of available options in the GUI automatically triggers the visualization representation to reassess constraint violations and update the color for each electrode accordingly.

In a further aspect, the invention relates to a non-transitory computer-readable medium storing computer executable code, wherein the computer executable code, when executed at one or more processors, causes a system to perform above functions for optimal active electrode selection and deactivation.

In one aspect, the invention relates a method for active electrode selection in a cochlear implant having an electrode array with a plurality of electrodes implanted in a cochlea of a living subject. The method comprises estimating an activation region (AR) of each electrode based on its distance to nerve sites; and automatically finding a set of active electrodes that do not have substantial AR overlap.

In one embodiment, said automatically finding the set of active electrodes is performed by a graph-based optimization algorithm.

In one embodiment, the graph-based optimization algorithm comprises defining a graph having a set of nodes, $N=\{n_i\}$, and edges, $E=\{e_{ij}\}$, wherein each node, $n_i$, represents an electrode in the electrode array, and edge $e_{ij}$ is a directed edge connecting electrode i to electrode j with cost; and determining an optimal path traversing edges connecting nodes with a minimum cumulative edge cost in the graph, wherein the nodes in the optimal path are corresponding to an optimal set of active electrodes.

In one embodiment, the nodes in the optimal path include a starting node and an ending node, wherein the starting node for the path is selected to be the most apical contact, and the ending node for the path is selected to be the electrode with PAR among the highest frequency nerves that can be effectively stimulated near the basal end of the cochlea.

In one embodiment, the ending node for the path is selected by defining a decision plane based on the one-to-one point correspondence between the segmentation in the patient image and an atlas image, wherein the decision plane is located where nerves with characteristic frequencies of about 15 kHz are located; and selecting the first electrode that lies apically to the decision plane as the ending node of the path.

In one embodiment, the edges E are defined to permit finding the optimal path with the minimum cumulative edge cost from the starting node to the ending node that represents the optimal set of active electrodes.

In one embodiment, hard constraints for edge $e_{ij}$ to exist and soft constraints for edge costs defined by a cost function $C(e_{ij})$ are used to ensure the minimal path corresponds to the optimal set of active electrodes.

In one embodiment, edge $e_{ij}$ exists only when first and second conditions are satisfied, wherein the first condition is i<j, which ensures the path traverses from the most apical electrode to a sequence of increasingly more basal neighbors until reaching the ending node, and the second condition is the AR for electrode j does not include the PAR for electrode i and vice versa.

In one embodiment, the AR of the electrode is a group of nerve sites that satisfy:

$$R = \frac{|E(\vec{x})|}{|E(PAR)|} = \frac{\|PAR - \vec{c}\|^2}{\|\vec{x} - \vec{c}\|^2} > \tau$$

wherein $|E(\vec{x})|$ and $|E(PAR)|$ are electric field strengths from the electrode c at a nerve site x of the group of nerve sites and its peak activation region (PAR), respectively, R is a ratio of the electric field strength from the electrode at the nerve site to that at the PAR, and $\tau$ is a threshold value to determine the AR for the electrode.

In one embodiment, the soft constraints are encoded in the cost function $C(e_{ij})$ that satisfies, $$C(e_{ij}) = \alpha d_i + (1-\alpha)\beta^{(j-i-1)}$$

wherein $d_i = \|PAR_i - \vec{c_\imath}\|$ is the distance from electrode i to its PAR, and $\alpha$ and $\beta$ are parameters with $0<\alpha<1$ and $\beta>1$, wherein the first term in the cost function rewards active electrodes that tend to have shorter distance to SG sites; and the second term in the cost function is used to ensure as many electrodes are active as allowable by the hard constraints, wherein when j=i+1, no electrodes are deactivated, when j>i+1, some electrodes are skipped in the path, which are to be deactivated; and when j>>i+1, a larger cost is assigned when deactivating multiple electrodes in sequence to discourage deactivations that result in large gaps in neural sites where little stimulation occurs.

In one embodiment, Djikstra's shortest-path algorithm is used to determine a global cost minimizing path in the graph, wherein the resulting path represents the set of electrodes that remains active, while electrodes not in the path is recommended for deactivation.

In another aspect, the invention relates to a method for automatically selecting electrodes to deactivate for image guided cochlear implant programming (IGCIP). The method comprises configuring the plurality of electrodes of the electrode array implanted in the cochlea of the living subject using the above method for active electrode selection.

In yet another aspect, the invention relates to a system comprising a CI device being implanted in a cochlea of a living subject, the CI device comprising an electrode array having a plurality of electrodes; and at least one computing device having one or more processors and a storage device storing computer executable code, wherein the computer executable code, when executed at the one or more processors, is configured to perform the above method for active electrode selection in the CI device.

In a further aspect, the invention relates to a non-transitory computer-readable medium storing computer executable code, wherein the computer executable code, when executed at one or more processors, causes a system to perform the above method for active electrode selection in a cochlear implant having an electrode array with a plurality of electrodes implanted in a cochlea of a living subject.

These and other aspects of the invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings illustrate one or more embodiments of the invention and, together with the written description, serve to explain the principles of the invention. The invention may be better understood by reference to one or more of these figures in combination with the detailed description of specific embodiments presented herein. The drawings described below are for illustration purposes only, and are not intended to limit the scope of the invention in any way. Wherever possible, the same reference numbers are used throughout the drawings to refer to the same or like elements of an embodiment.

DETAILED DESCRIPTION OF THE INVENTION

Figure 1A:
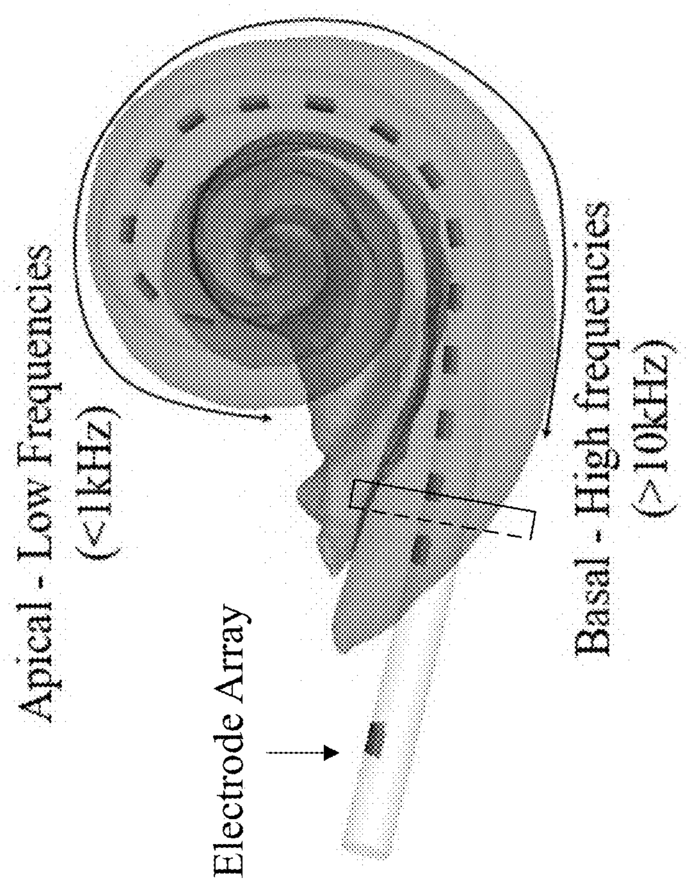
FIG. 1A is a 3D representation of the cochlea (red) and the inserted electrode array (gray). The modiolus containing the spiral ganglion (SG) cells is shown in green.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this invention will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that, as used in the description herein and throughout the claims that follow, the meaning of "a", "an", and "the" includes plural reference unless the context clearly dictates otherwise. Also, it will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending of the particular orientation of the figure. Similarly, if the device in one of the figures. is turned over, elements described as "below" or "beneath" other elements would then be oriented "above" the other elements. The exemplary terms "below" or "beneath" can, therefore, encompass both an orientation of above and below.

It will be further understood that the terms "comprises" and/or "comprising," or "includes" and/or "including" or "has" and/or "having", or "carry" and/or "carrying," or "contain" and/or "containing," or "involve" and/or "involving, and the like are to be open-ended, i.e., to mean including but not limited to. When used in this invention, they specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the invention, and will not be interpreted in an idealized or overly formal sense unless expressly so defined herein.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the phrase "at least one of A, B, and C" should be construed to mean a logical (A or B or C), using a non-exclusive logical OR. It should be understood that one or more steps within a method may be executed in different order (or concurrently) without altering the principles of the invention.

As used herein, the term "activation region" or its acronym, "AR" of an electrode refers to a group of nerve sites that receive significant stimulation when the electrode is activated.

As used herein, the term "peak activation region" or its acronym, "PAR" of an electrode refers to a nerve site most likely to be stimulated by the electrode, which is generally assumed to be the site closest to the electrode.

As used herein, the term "channel interaction" refers to overlapping stimulation of a same nerve site by multiple electrodes, which can lead to poorer hearing outcomes. For example, if the PAR of one electrode falls within the AR of another electrode, this pair of electrodes is considered to have the channel interaction that may affect hearing outcomes.

The description below is merely illustrative in nature and is in no way intended to limit the invention, its application, or uses. The broad teachings of the invention can be implemented in a variety of forms. Therefore, while this invention includes particular examples, the true scope of the invention should not be so limited since other modifications will become apparent upon a study of the drawings, the specification, and the following claims. For purposes of clarity, the same reference numbers will be used in the drawings to identify similar elements. It should be understood that one or more steps within a method may be executed in different order (or concurrently) without altering the principles of the invention.

The cochlear implant is neural prosthesis including an implanted electrode array and an external processor that is designed to directly stimulate auditory nerve fibers to induce the sensation of hearing in those who have experienced severe hearing loss. After surgical implantation, the processor needs to be programmed to assign power and a frequency range to each electrode of the array so as to produce electrically-induced hearing. However, channel interactions, i.e., overlapping stimulation of the same nerve sites by multiple electrodes, may occur and lead to poorer hearing outcomes. Modifying a patient's active set of electrodes to eliminate interactions is one method to address the channel interactions.

To determine if two electrodes have too much overlapping stimulation, first, the nerve site most likely to be stimulated by an electrode can be defined as its peak activation region (PAR), a subset of the larger activation region (AR), which includes all nerve sites likely to receive significant stimulation from that electrode, i.e., its spread of excitation. If an electrode's AR is defined as the region containing ANFs that should only be substantially activated by that electrode, then deleterious channel interactions can be defined as any case in which the PAR of one electrode falls within the AR of another electrode. A seemingly obvious solution is to eliminate this overlap by decreasing the spread of excitation. The width of the spread of excitation is directly related to the amount of current delivered to the electrode that is necessary to induce comfortable levels of perception in that region. As the distance between an electrode and the modiolus increases, more current is needed to achieve the same level of perception, and greater current results in a wider AR. Therefore, eliminating channel interactions is not as simple as reducing current levels until there is no overlapping stimulation, as doing so could also have significant impacts on a patient's hearing.

An alternative approach deactivates at least one electrode in a set of electrodes with significant overlap in stimulation. To accurately determine these sets of electrodes, an audiologist would need to know the location of each electrode in the array. Without the resources to obtain this information, they typically must assume optimal placement of the array, despite the reality that with current surgical techniques, the array is inserted blindly, often resulting in sub-optimal placement. Because prior research supports the conclusion that many aspects of array location significantly impact hearing outcomes, it is imperative to develop tools that can provide this information to clinicians. In previous research, our group has developed a series of automated methods for image-guided cochlear implant programming (IGCIP). These methods allow us to segment a patient's cochlear anatomy from computed tomography (CT) images by fitting a high-resolution anatomical model created from micro-CT images of cadaver *cochleae* to the patient images. Methods also have been developed to localize the electrode array, allowing creation of a three-dimensional model of that patient's cochlea and array placement, an example of which is shown in FIG. 1A. These techniques enable audiologists to evaluate multiple spatial features, including distance of the array to the modiolus, insertion depth of the array, and any undesirable placements, e.g., translocation from the scala tympani to the scala vestibuli.

Figure 2:
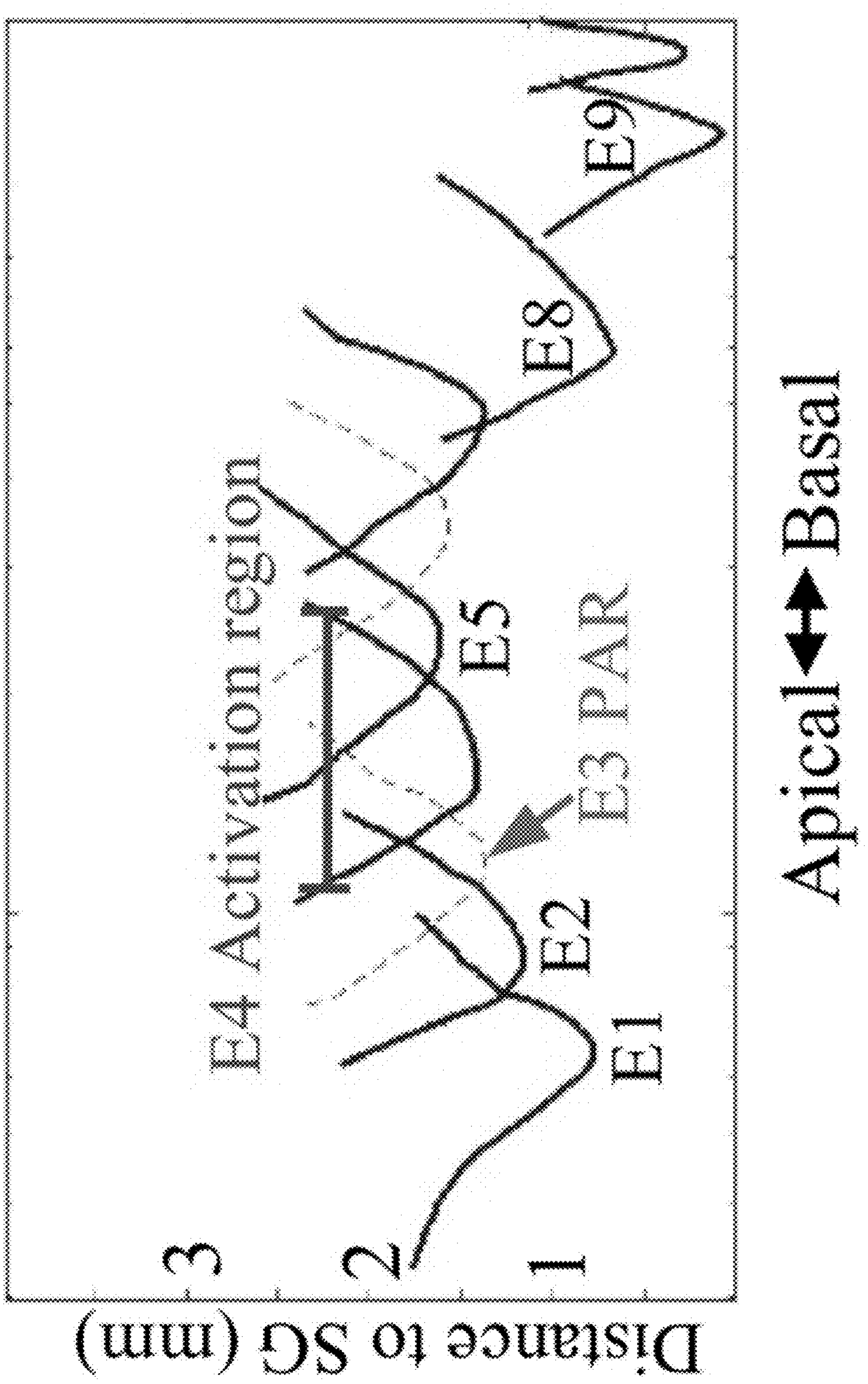
FIG. 2 shows DVF curves showing a deactivation plan. Active electrodes are represented by solid blue lines, and deactivated electrodes by dashed gray lines.

Our group uses the spatial information provided by the IGCIP techniques to estimate an electrode's spread of excitation as the distance from that electrode to nerve sites. We visualize this in a format of the distance-vs-frequency, or DVF, curves, an example of which is shown in FIG. 2. In a set of DVF curves, each curve corresponds to one electrode in the array, where each point along a curve represents the distance from the associated electrode to different nerve sites. The vertical axis indicates this distance in millimeters, and the horizontal axis spans the frequency range associated with the nerve sites of the cochlea, displayed on a log scale. This plot shows the place frequencies of the nerve sites most likely to be stimulated by an electrode, and by extension, the nerve sites most likely to receive overlapping stimulation from multiple electrodes. When using the DVF curve format, the PAR is easy to identify, as it is assumed to be the closest nerve site to an electrode, i.e., the minimum of that electrode's DVF curve. However, it is more difficult to precisely identify the entirety of the AR because its width is not static across the array, with more distant electrodes typically having wider ARs than closer electrodes. Since it is not quantitatively estimated and displayed, it is also subjective to the reviewer's estimation. Learning to read DVF curves and utilizing them to accurately, consistently select optimal electrode array deactivation plans can be difficult and time-consuming.

In view of the foregoing, one of the objectives of the invention is to provide an alternative visualization to the DVF curves that removes much of this subjectivity by visualizing channel overlap using a model of estimated electric field strength. The new visualization is termed as the activation region overlap (ARO) image, and permits visualizing the relationship between the ARs of each electrode in the electrode array.

In one aspect, the invention relates to a method for active electrode selection in a cochlear implant having an electrode array with a plurality of electrodes implanted in a cochlea of a living subject. The method includes estimating an AR of each electrode based on its distance to nerve sites; presenting the AR in a visualization representation, wherein each electrode is represented by a bar having a width or length representing the AR; identifying electrodes having substantial AR overlap if the AR of one electrode overlaps substantially with the AR bar of another electrode; and selecting and deactivating at least one of the identified electrodes with substantial AR overlap.

In one embodiment, the AR of the electrode is a group of nerve sites that satisfy $$R = \frac{|E(\vec{x})|}{|E(PAR)|} = \frac{\|PAR - \vec{c}\|^2}{\|\vec{x} - \vec{c}\|^2} > \tau$$

wherein $|E(\vec{x})|$ and $|E(PAR)|$ are electric field strengths from the electrode c at a nerve site x of the group of nerve sites and the PAR, respectively, R is a ratio of the electric field strength from the electrode at the nerve site to that at the PAR, and $\tau$ is a threshold value used to determine the AR for each electrode.

In one embodiment, the threshold value $\tau$ defines a tolerance for the activation region overlapping between electrodes, and large values for the threshold value $\tau$ indicate a greater tolerance for the activation region overlapping between the electrodes, producing a narrower AR, while small values for the threshold value $\tau$ indicate less tolerance for the activation region overlapping between the electrodes, resulting in a larger AR.

In one embodiment, $\tau=0.5$. It should be appreciated that other values of t can also be utilized to practice the invention.

In one embodiment, the visualization representation has a horizontal axis representing characteristic frequencies (CF) of the spiral ganglion, and a vertical axis representing each electrode of the electrode array, with each horizontal colored bar associated with one electrode.

In one embodiment, the most apical electrode is located at the bottom of the visualization representation, and the most basal electrode is located at the top of the visualization representation.

In one embodiment, said selecting and deactivating step further comprises deactivating any electrode with a PAR with characteristic frequency greater than 15 kHz.

In one embodiment, the graph-based method further includes coding operation states of each electrode with different colors in the visualization representation, comprising coding the electrode with a first color if it is activated and does not have significant interaction with another electrode; a second color if it is deactivated; a third color if it is activated but has significant interaction with another electrode; or a fourth color if it is deactivated but could be activated without having significant interaction with another electrode.

In one embodiment, the visualization representation comprises a graphical user interface (GUI), configured such that changing any of available options in the GUI automatically triggers the visualization representation to reassess constraint violations and update the color for each electrode accordingly.

In another aspect of the invention the method comprises estimating an AR of each electrode based on its distance to nerve sites; and automatically finding a set of active electrodes that do not have substantial AR overlap.

In one embodiment, said automatically finding the set of active electrodes is performed by a graph-based optimization algorithm.

In one embodiment, the graph-based optimization algorithm comprises defining a graph having a set of nodes, $N=\{n_i\}$, and edges, $E=\{e_{ij}\}$, wherein each node, $n_i$, represents an electrode in the electrode array, and edge $e_{ij}$ is a directed edge connecting electrode i to electrode j with cost; and determining an optimal path traversing edges connecting nodes with a minimum cumulative edge cost in the graph, wherein the nodes in the optimal path are corresponding to an optimal set of active electrodes.

In one embodiment, the nodes in the optimal path include a starting node and an ending node, wherein the starting node for the path is selected to be the most apical contact, and the ending node for the path is selected to be the electrode with PAR among the highest frequency nerves that can be effectively stimulated near the basal end of the cochlea.

In one embodiment, the ending node for the path is selected by defining a decision plane based on the one-to-one point correspondence between the segmentation in the patient image and an atlas image, wherein the decision plane is located where nerves with characteristic frequencies of about 15 kHz are located; and selecting the first electrode that lies apically to the decision plane as the ending node of the path.

In one embodiment, the edges E are defined to permit finding the optimal path with the minimum cumulative edge cost from the starting node to the ending node that represents the optimal set of active electrodes.

In one embodiment, hard constraints for edge $e_{ij}$ to exist and soft constraints for edge costs defined by a cost function $C(e_{ij})$ are used to ensure the minimal path corresponds to the optimal set of active electrodes.

In one embodiment, edge $e_{ij}$ exists only when first and second conditions are satisfied, wherein the first condition is $i<j$, which ensures the path traverses from the most apical electrode to a sequence of increasingly more basal neighbors until reaching the ending node, and the second condition is the AR for electrode j does not include the PAR for electrode i and vice versa.

In one embodiment, the AR of the electrode is a group of nerve sites that satisfy:

$$R = \frac{|E(\vec{x})|}{|E(PAR)|} = \frac{\|PAR - \vec{c}\|^2}{\|\vec{x} - \vec{c}\|^2} > \tau$$

wherein $|E(\vec{x})|$ and $|E(PAR)|$ are electric field strengths from the electrode $\vec{c}$ at a nerve site $\vec{x}$ of the group of nerve sites and its peak activation region (PAR), respectively, R is a ratio of the electric field strength from the electrode at the nerve site to that at the PAR, and $\tau$ is a threshold value to determine the AR for the electrode.

In one embodiment, the soft constraints are encoded in the cost function $C(e_{ij})$ that satisfies, $$C(e_{ij}) = \alpha d_i + (1-\alpha)\beta^{(j-i-1)}$$

wherein $d_i = |PAR_i - \vec{c_i}||$ is the distance from electrode i to its PAR, and $\alpha$ and $\beta$ are parameters with $0<\alpha<1$ and $\beta>1$, wherein the first term in the cost function rewards active electrodes that tend to have shorter distance to SG sites; and the second term in the cost function is used to ensure as many electrodes are active as allowable by the hard constraints, wherein when $j=i+1$, no electrodes are deactivated, when $j>i+1$, some electrodes are skipped in the path, which are to be deactivated; and when $j>>i+1$, a larger cost is assigned when deactivating multiple electrodes in sequence to discourage deactivations that result in large gaps in neural sites where little stimulation occurs.

In one embodiment, Djikstra's shortest-path algorithm is used to determine a global cost minimizing path in the graph, wherein the resulting path represents the set of electrodes that remains active, while electrodes not in the path is recommended for deactivation.

In yet another aspect, the invention relates to a method for automatically selecting electrodes to deactivate for image guided cochlear implant programming (IGCIP), comprising configuring the plurality of electrodes of the electrode array implanted in the cochlea of the living subject using the above disclosed method.

In a further aspect, the invention relates to a system comprising a CI device being implanted in a cochlea of a living subject, the CI device comprising an electrode array having a plurality of electrodes; and at least one computing device having one or more processors and a storage device storing computer executable code, wherein the computer executable code, when executed at the one or more processors, is configured to perform the above disclosed method.

It should be noted that all or a part of the steps according to the embodiments of the invention is implemented by hardware or a program instructing relevant hardware.

Yet another aspect of the invention provides a non-transitory computer readable storage medium/memory which stores computer executable instructions or program codes. The computer executable instructions or program codes enable a system to complete various operations in the above disclosed method for optimal active electrode selection in a cochlear implant having an electrode array with a plurality of electrodes implanted in a cochlea of a living subject. The storage medium/memory may include, but is not limited to, high-speed random access medium/memory such as DRAM, SRAM, DDR RAM or other random access solid state memory devices, and non-volatile memory such as one or more magnetic disk storage devices, optical disk storage devices, flash memory devices, or other non-volatile solid state storage devices.

Without intent to limit the scope of the invention, examples and their related results according to the embodiments of the invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

EXAMPLE 1 a Graph-Based Method for Optimal Active Electrode Selection in Cochlear Implants The cochlear implant (CI) is a neural prosthetic that is the standard-of-care treatment for severe-to-profound hearing loss. The CI includes an electrode array inserted into the cochlea that electrically stimulate auditory nerve fibers to induce the sensation of hearing. Competing stimuli occur when multiple electrodes stimulate the same neural pathways. This is known to negatively impact hearing outcomes. Previous research has shown that image-processing techniques can be used to analyze the CI position in CT scans to estimate the degree of competition between electrodes based on the CI user's unique anatomy and electrode placement. The resulting data permits an algorithm or expert to select a subset of electrodes to keep active to alleviate competition. Expert selection of electrodes using this data has been shown in clinical studies to lead to significantly improved hearing outcomes for CI users.

Currently, we aim to translate these techniques to a system designed for worldwide clinical use, which mandates that the selection of active electrodes be automated by robust algorithms. Previously proposed techniques produce optimal plans with only 48% success rate. In this exemplary study, we disclose a new graph-based approach. We design a graph with nodes that represent electrodes and edge weights that encode competition between electrode pairs. We then find an optimal path through this graph to determine the active electrode set. Our method produces results judged by an expert to be optimal in over 95% of cases. This technique could facilitate widespread clinical translation of image-guided cochlear implant programming methods.

In a subject without hearing loss, sounds reaching the cochlea would be transduced to electrical impulses that stimulate auditory nerve fibers. The nerve fibers are tonotopically organized, meaning that activation of nerve fibers located in different regions of the cochlea create the sensation of different sound frequencies. The frequency for which a nerve fiber is activated in natural hearing is called its characteristic frequency. As such, in natural hearing nerve fibers are activated when their characteristic frequencies are present in the incoming sound.

In a patient with hearing loss, sounds no longer properly activate auditory nerve fibers. The purpose of CI is to bypass the natural transduction mechanisms and provide direct electrical stimulation of auditory nerve fibers to induce hearing sensation. A CI includes an electrode array that is surgically implanted in the cochlea (see FIG. 1A) and an external processor. The external processor translates auditory signals to electrical impulses that are distributed to the electrodes in the array according to the patient's MAP, which is the set of processor instructions determined by an audiologist in an attempt to produce optimal hearing outcomes. Tunable parameters in a patient's MAP include the active set of electrodes, the stimulation level of each electrode, and a determination of which electrodes should be activated when a particular frequency of sound is detected by the processor. Research indicates that the locations of electrodes within the cochlea impact the quality of hearing outcomes. Most patients have less-than-optimal electrode array placement, so customizing the patient's MAP is critical for optimizing hearing outcomes. Previous studies have proposed methods for segmenting cochlear anatomy and electrode arrays from pre- and post-operative computed tomography (CT) images, permitting creation of 3D models of cochlear structures.

Research has also shown that the spatial information garnered from these methods can be used to estimate channel interactions between electrodes. Channel interaction occurs when nerves, which naturally are activated for a finely tuned sound frequency, receive overlapping stimulation from multiple electrodes, corresponding to multiple frequency channels. This creates spectral smearing artifacts that lead to poorer hearing outcomes. Manipulating a subject's MAP to modify the active electrode set and the stimulation patterns can reduce these effects. The spatial relationship between electrodes and neural sites is a driving factor for channel interaction. Assuming the electrodes behave similarly to point charges in a homogeneous medium, which is a common assumption given the electrodes are monopolar sources that sink current to a far away ground, Coulomb's law mandates that electric field strength, $E(\vec{x})$, at location $\vec{x}$ is inversely proportional with squared distance between $\vec{x}$ and the electrode location $\vec{c}$.

$$|E(\vec{x})| \propto \frac{1}{\|\vec{x}-\vec{c}\|^2} \tag{1}$$

Figure 1B:
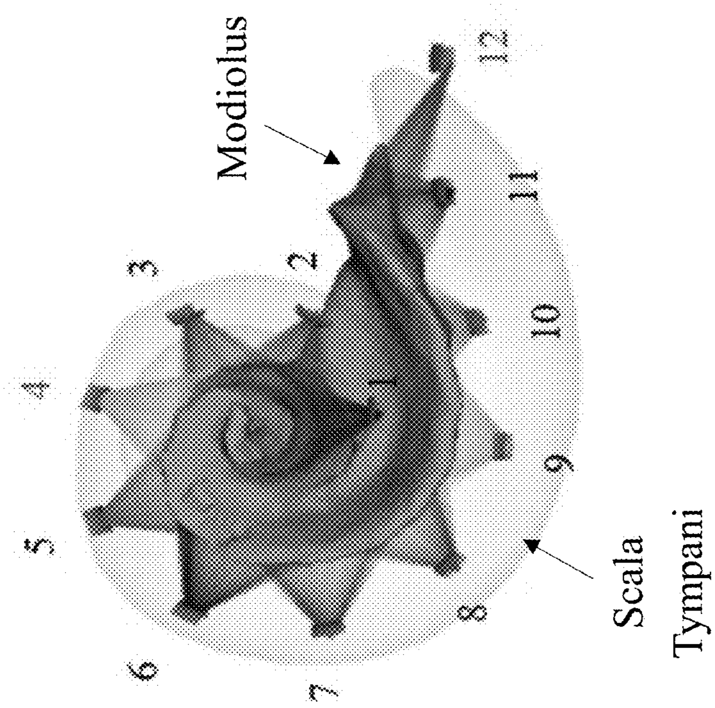
FIG. 1B shows estimated spread of excitation for each electrode in the array shown against the modiolus. Electrodes are numbered 1-12 from most apical to most basal.

Thus, as shown in FIG. 1B, when an electrode is close to neural sites (e.g., E8-E10), relatively little current is needed to activate nearby nerves, resulting in relatively little spread of excitation. However, when an electrode is distant to neural sites, neural activation requires broad stimulation patterns due to electrical current spread at greater distance. When two electrodes are close together and both distant to neural sites (e.g., E5-E6), they create substantial stimulation overlap, resulting in channel interaction.

One method of visualizing the spatial relationship between electrodes and neural sites to determine when channel interaction occurs is to use distance vs. frequency (DVF) curves. These curves represent the distance from the auditory nerve spiral ganglion (SG) cells, which are the most likely target of electrical stimulation, to nearby electrodes (see FIG. 2). The characteristic frequencies of the nerve fiber SG sites are shown on the horizontal axis, and the distance to electrodes near to those neural sites are shown with the height of an individual curve for each electrode on the vertical axis. This simplifies the process of determining which nerve pathways are likely to be stimulated by a given electrode and where two electrodes might stimulate the same region. An electrode is most likely to stimulate the nerves it is closest to, as indicated by the horizontal position of the minimum of the curve. We refer to these nerves as having SGs located in the peak activation region (PAR) for the electrode. Determining which nerves are stimulated by multiple electrodes requires making additional assumptions about the spread of excitation of each contact.

In this exemplary example, we use Eqn. (1) to estimate electric field strength, and assume the activation region for an electrode includes any nerves with SG sites x that satisfy:

$$\frac{|E(\vec{x})|}{|E(PAR)|} = \frac{\|PAR-\vec{c}\|^2}{\|\vec{x}-\vec{c}\|^2} > \tau \tag{2}$$

which requires that the strength of the electric field in SGs must be greater than a certain fraction, $\tau$, of the electric field in the PAR for those nerves to be considered active. This is equivalent to ensuring the ratio of squared distance from the PAR to the electrode to the square distance from another nerve SG site to the electrode is greater than $\tau$. The DVF curves, as shown in FIG. 2, permit visually assessing the activation region for each contact. The activation region is defined by the width of the curve for which $\sqrt{\tau}$ times the curve height, $\sqrt{\tau}\|\vec{x}-\vec{c}\|$, is less than or equal to the minimum curve height, $\|PAR-\vec{c}\|$.

If substantial overlap of activation regions exists between neighboring electrodes, some electrodes may be selected for deactivation to reduce overlap. This is one approach for image-guided CI programming (IGCIP), i.e., a method that uses image information to assist audiologists optimize programming of CIs. The original technique for selecting the deactivation set required an expert to manually review each case and determine the optimal solution based on the information in this DVF curves. This process is not ideal for clinical translation as it can be time-consuming and requires expertise. Automated methods have been developed to eliminate the need for expert review, which either rely on an exhaustive search to optimize a cost function or attempt to learn to replicate expert deactivation patterns using template matching. However, as presented below, the current state-of-the-art method leads to optimal results in only 48% of cases, which is insufficiently reliable for widespread clinical translation.

In this example, we present an automated method for determining the active electrode set as a minimum cost path in a custom-designed graph. As our results show, the method is significantly more robust in finding optimal deactivation plans compared to the state-of-the-art method and could facilitate automated clinical translation of IGCIP methods.

Methods

The dataset used in this study includes 83 cases for which we have patient-specific anatomical data that can be used to generate the DVF curves and electrode deactivation plans generated by the current state-of-the-art techniques and the method we previously proposed. All cases use an implant from one of three manufacturers: MED-EL (MD) (Innsbruck, Austria), Advanced Bionics (AB) (Valencia, California), and Cochlear (CO) (New South Wales, Australia). Of the cases we studied, 24 utilized an implant from MD, 32 from AB, and 27 from CO.

Graph Definition: We propose a graph, G={N, E}, as a set of nodes N and edges E. Each node N represents an electrode in the array, and an optimal path traversing edges connecting nodes with minimum cumulative edge cost in this graph will include nodes corresponding to the recommended set of active electrodes. Electrodes corresponding to nodes not included in the path will be recommended for deactivation. Using this approach, we need to define the edge structure, edge costs, and starting and ending nodes of the path in the graph.

The starting node for the path is chosen to be the most apical contact (see FIG. 1A). This is because it is well known in the audiology community that deactivating the most apical contact, which has PAR at the lowest frequency nerves, creates perceived frequency upshifts that are generally bad for hearing outcomes. Thus, it is desirable for this electrode to always be active and included in the optimal path. Similarly, the ending node should be chosen to be the electrode with PAR among the highest frequency nerves that can be effectively stimulated near the basal end of the cochlea. It is also well known that electrodes outside the cochlea as well as those near the entrance of the cochlea are typically ineffective in stimulating auditory nerves. Since we use the active-shape-model based segmentation approach to segment the cochlea, we rely on the one-to-one point correspondence between the segmentation in the patient image and an atlas image to define a decision plane (shown in FIG. 1A). The plane is located where nerves with characteristic frequencies of 15 kHz are located. The first electrode that lies apically to this plane is considered the ending node of the path.

Figure 3:
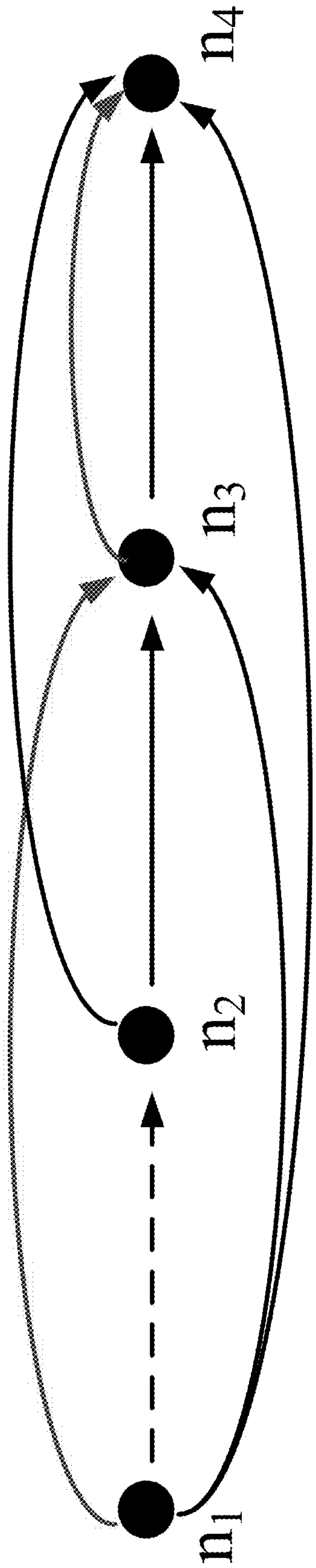
FIG. 3. Visualization of our graph design. Each node is indicated with a black circle and is labeled with a node number $n_i$. Dotted lines indicate invalid edges, and solid lines indicate valid edges. Red lines indicate an example path through the graph.

The edges E must be defined to permit finding a minimum edge cost path from the starting to the end node that represents the optimal set of active electrodes. The structure of E that we propose is shown in FIG. 3. Edge $e_{ij}$ is a directed edge connecting electrode i to electrode j with cost $C(e_{ij})$. Hard constraints (whether $e_{ij}$ exists) and soft constraints (edge costs defined by a cost function $C(e_{ij})$) are used to ensure the minimal path corresponds to the optimal active electrode set. Two necessary conditions must be met for $e_{ij}$ to exist. First, $e_{ij}$ only exists if $i<j$. This ensures the path traverses from the most apical electrode, E1, to a sequence of increasingly more basal neighbors until reaching the ending node. As seen in FIG. 3, directed edges only exist connecting nodes to higher numbered nodes. Second, we encode a maximum allowable amount of activation region overlap between sequential active electrodes in the path as a hard constraint. We use Eqn. (2) to define the activation region for each electrode and let $\tau=0.5$ in our experiments. We then define overlap acceptable if the activation region for electrode j does not include the PAR for electrode i and vice versa. Thus, if the region most likely to be activated by an electrode (its PAR) is also active by another electrode, too much overlap is occurring, in which case $e_{ij}$ does not exist. For example, in FIG. 2 the PAR for E3 falls within the activation region for E4, therefore $\nexists\, e_{34}$. An example of such a scenario is shown in the exemplary graph in FIG. 3 with edge $e_{12}$. With $n_1$ and $n_2$ exhibiting too much overlap, $\nexists\, e_{12}$, and thus a path from $n_1$ must skip $n_2$ and instead traverse directly to $n_3$ or $n_4$. One example allowable path in this graph is shown in red.

Soft constraints are encoded in an edge cost function, $$C(e_{ij}) = \alpha d_i + (1-\alpha)\beta^{(j-i-1)} \tag{3}$$

where $d_i=\|PAR_i-\vec{c_i}\|$ is the distance from electrode i to its PAR, and $\alpha$ and $\beta$ are parameters. The second term in the cost function is used to ensure as many electrodes are active as allowable by the hard constraints, since when $j=i+1$, no electrodes are deactivated, but when $j>i+1$, some electrodes are skipped in the path, indicating they will be deactivated, and, assuming $\beta>1$, a higher cost is associated with this. Further, a larger cost is assigned when deactivating multiple electrodes in sequence, i.e., when $j>>i+1$, to discourage deactivations that result in large gaps in neural sites where little stimulation occurs. Larger values of $\beta$ result in greater values for this penalty. The first term in Eqn. (3) rewards active electrodes that tend to have lower distance to SG sites. The parameter $\alpha$ controls the relative contribution of the two terms.

Using this graph, Djikstra's shortest-path algorithm can determine the global cost minimizing path in our graph. This resulting path represents the set of electrodes that should remain active, while electrodes not in the path will be recommended for deactivation.

Validation Study: Ideally, we would have an expert determine the optimal deactivation plan for each of the 83 cases in our dataset and measure the rate at which the algorithm produces the optimal plan. However, for a given case, it is possible that there are a number of deactivation configurations that could be considered equally optimal, and it is difficult to determine a complete set of equally optimal plans. Thus, to assess the performance of our method, we instead implemented a masked expert review study to assess optimality of the results of our algorithm compared to the current state-of-the-are algorithm and control plans for each case. In this study, an expert reviewer was presented with a graphical representation of the DVF curves for each case, showing the planned active and deactivated electrodes, similarly to FIG. 2. The reviewer was instructed to determine whether each plan was optimal, i.e., whether the reviewer would adjust anything in the presented plan. Three sets of plans for each case were presented in this study. The first set includes the results from our proposed method using parameters $\alpha=0.5$ and $\beta=4$. These parameter values were determined heuristically using DVF curves from 10 cases not included in the validation set. The second set is the deactivation result from the method described in Zhao et al. (2016) [19]. The final set includes control plans, manually created by a second expert, where the active set is close to acceptable, but suboptimal. The inclusion of the control plans is used to indicate if the reviewer has a bias toward rating plans as optimal, e.g., if a large number of the control cases are rated as optimal, the reviewer likely has such a bias. These three sets of plans were presented one at a time in random order. The reviewer was masked to the source of each plan in order to prevent bias towards any method.

Parameter Sensitivity Analysis: We performed a parameter sweep to assess the sensitivity of the parameters in our cost function across a set of values around the heuristically determined values of $\alpha=0.5$ and $\beta=4$ used above in the validation study. We used our proposed method to determine the active electrode set with parameter $\alpha$ in the range of 0.1-0.9 with step size of 0.1 and $\beta$ in the range of 2-6 with a step size of 0.5. This resulted in 81 different parameter combinations for each case. We then used the Hamming distance metric to compare the resulting plan to the plan evaluated in the validation study. Large differences would indicate greater sensitivity of the method to the parameters.

Results and Discussion

The results of our validation study are shown in Table 1. Our reviewer judged 79 of the plans generated using our proposed method to be optimal, rejecting only four cases.

Only 40 of the plans from the previous method described in Zhao et al. (2016) were rated optimal, and none of the control plans were marked optimal. Accepting none of the control plans indicates that our expert reviewer is not biased toward accepting configurations and can accurately distinguish between optimal and close-to-optimal plans. We used McNemar mid-p tests to assess the accuracy of our plan to produce an optimal result versus that of the current state-of-the-art method in Zhao et al. (2016) [19] as well as the control method. We found that the difference in success rates between the two methods and between the proposed and control method were highly statistically significant ($p<10^{-9}$).

Figure 4A:
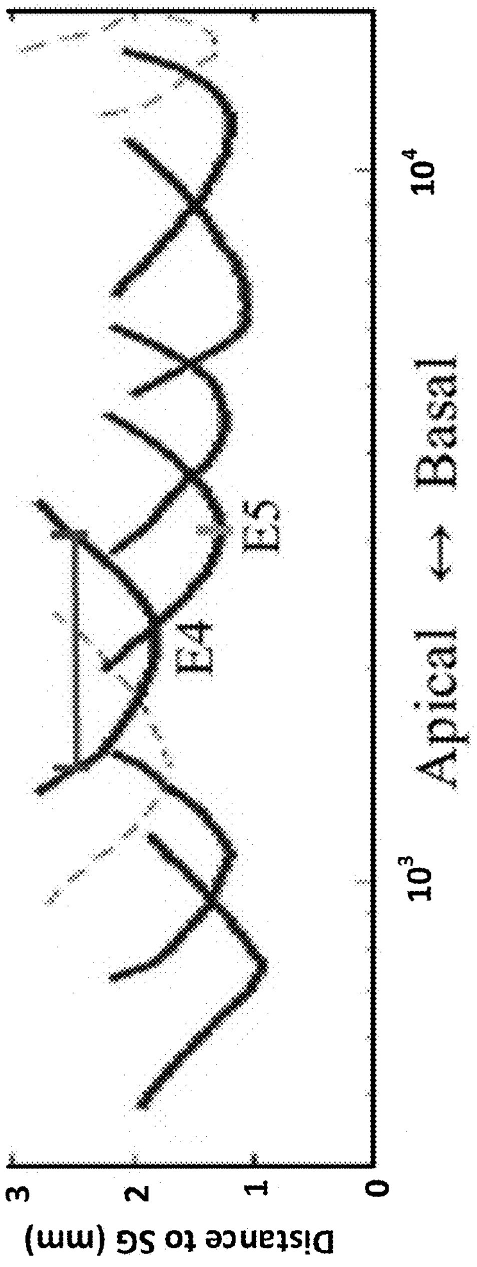
FIG. 4A is a rejected plan generated using our proposed method.
Figure 4B:
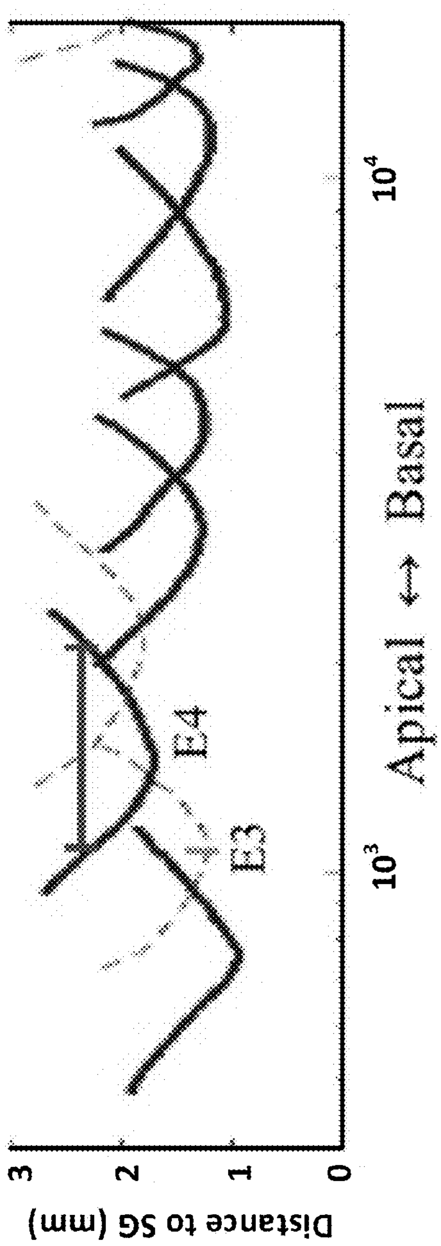
FIG. 4B is a rejected plan generated using the method from Zhao et al. (2016) [19], showing the same case as FIG. 4A.

Inspecting the four cases where the proposed deactivation plan was rejected, the reviewer noted that the plans for these cases were actually optimal, and the rejection in each case was due to erroneous reading of the DVF curves when the amount of activation region overlap between electrodes was very close to the acceptable overlap decision threshold. DVF curves for one such case are shown in FIG. 4A, along with the deactivation plan suggested by Zhao et al. (2016) in FIG. 4B. The plan from the proposed algorithm in FIG. 4A was rejected because the reviewer mistakenly believed the PAR for E5 (green) fell within the activation region for E4 (red).

Note that the hard constraints imposed by our proposed method guarantee plans that are free of this type of error, which is a significant benefit of graph-based, compared to other optimization methods. The plan from algorithm of Zhao et al. (2016) in FIG. 4B was correctly judged to be unacceptable because the PAR for E3 (green) falls outside the activation region for E4 (red), meaning E3 should be active.

TABLE 1

Validation study results.

| | Proposed | Algorithm from Zhao et al. (2016) [19] | Control |
|---|---|---|---|
| Optimal | 79 | 40 | 0 |
| Non-Optimal | 4 | 43 | 83 |

Figure 5:
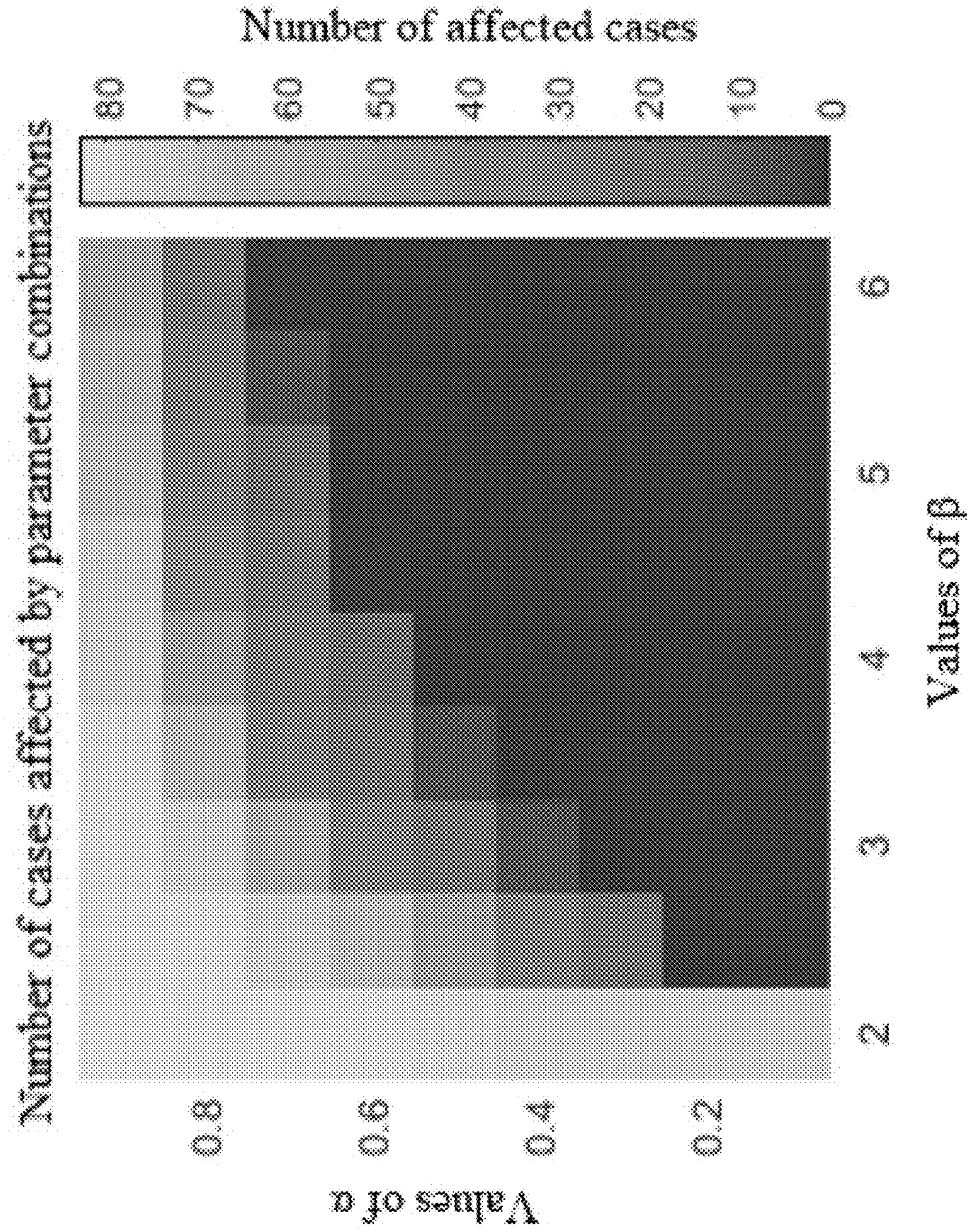
FIG. 5. Parameter sensitivity test results. Higher values indicate a greater number of plans with differences from the originally generated plans, where $\alpha=0.5$ and $\beta=4$
Figure 6:
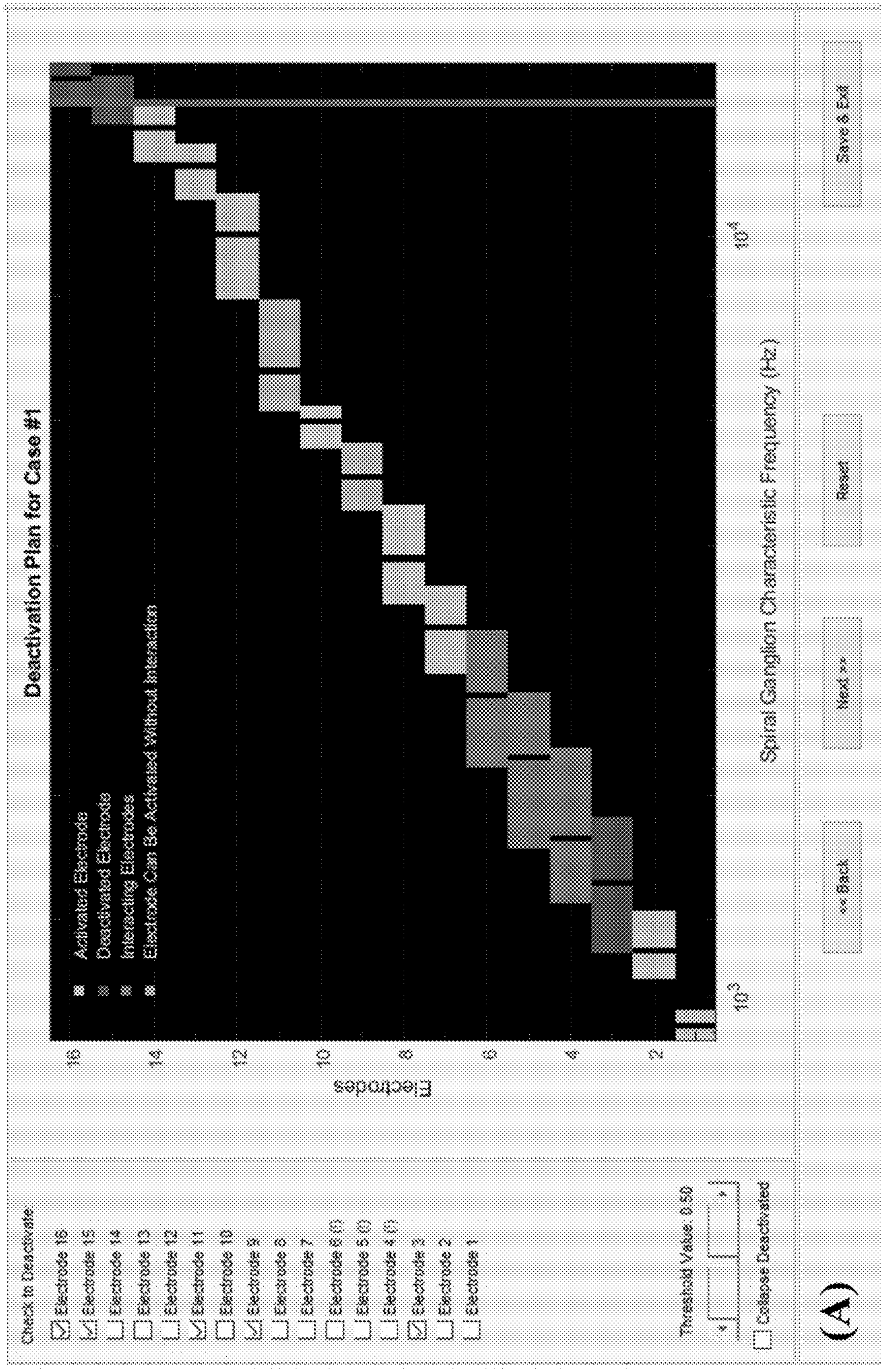
FIG. 6 is an exemplary ARO image, showing the same case (No. 1) from FIG. 2 with a modified deactivation plan that ignores electrodes determined to have significant overlap. Green: activated electrodes. Gray: deactivated electrodes. Orange: activated electrodes that have too much overlap with another electrode. Lavender (pink): electrodes that are deactivated but could be activated without having significant overlap with another electrode.

The results of our parameter sensitivity study are shown in FIG. 5. We found that our method was relatively insensitive to low values for α and high values for β, i.e., the deactivation plan did not change from the α=0.5, β=4 solution used in the validation study in this region of the parameter space. However, large number of plans changed when a was high or β was low. Since our validation study revealed that α=0.5, β=4 produced optimal solutions, changes in many plans indicates that those configurations likely produce sub-optimal results. This finding is reasonable since, when β is low or a is high, deactivating numerous electrodes in sequence is not properly penalized in the cost function.

Conclusion

In this study, we presented an automated graph-based approach for selecting active electrode sets in CIs. Automated selection methods reduce the time required to develop a patient-specific plan and remove the necessity for an expert reviewer to manually select the active electrodes from a set of DVF curves. Clinical translation of IGCIP techniques requires that our developed methods be robust and reliable to maximize positive hearing outcomes in patients. Our approach utilized spatial information available from previous techniques for segmenting cochlear structures and electrode arrays. We used this information to develop a graph-based solution for selecting an optimal active electrode set. To validate our results, we asked an expert reviewer to rate electrode configurations as optimal or non-optimal, where for a plan to be considered optimal, the reviewer would make no changes to that plan. 95.2% of plans created from our method were accepted as optimal, compared to only 48.2% of plans generated using the current state-of-the-art technique. Further, post-evaluation review revealed that the four rejected plans from our proposed method were actually optimal. These results suggest that our method is significantly more robust than the current state-of-the-art method and could facilitate widespread, automated clinical translation of IGCIP methods for CI programming. In the future, we plan to evaluate our method in a clinical study to confirm that the results of our method produce improved hearing outcomes for CI recipients in practice. This study would examine improvements in hearing outcomes for subjects relative to their current implant configuration over the course of several weeks by collecting data before reprogramming and again after a 3 to 6-week adjustment period to the new electrode configuration. Following successful clinical confirmation of our method, we will perform a multi-site study to assess clinically translating this method to other institutions.

EXAMPLE 2

Image-Guided Visualization of Channel Interaction for Cochlear Implant Programming The cochlear implant is neural prosthesis including an implanted electrode array and an external processor that is designed to directly stimulate auditory nerve fibers to induce the sensation of hearing in those who have experienced severe hearing loss. After surgical implantation, audiologists program the processor with settings intended to produce optimal hearing outcomes. The likelihood of achieving optimal outcomes increases when audiologists are provided with tools that assist them in making objective decisions based on the patient's own anatomy and the surgical placement of the array. A visualization tool currently in use, called distance-vs-frequency (DVF) curves, can be used to estimate channel interactions between electrodes. Although the information presented in this visualization is objective, an audiologist's decisions are subject to their own subjective interpretation of these curves.

In this exemplary study, a new visualization technique, termed activation region overlap (ARO) image, is disclosed. The ARO is designed to remove the subjectivity of visually assessing channel interactions between electrodes. A multi-reviewer study of 15 cases shows that plans created using this new visualization are more consistent, are created more efficiently, and are rated as optimal more frequently than plans generated using the DVF curves.

Methods

Defining the Activation Region: Research on electro-anatomical models (EAMs) of the implanted cochlea has shown modeling a CI electrode as a simple point charge in a homogeneous medium yields similar results to more sophisticated finite-element models with assumed tissue resistivity values falling within the range of known tissue resistivity variability. Therefore, the point charge model is used to estimate the strength of an electric field due to an electrode c at a specified nerve site $\vec{x}$, which can be calculated according to Coulomb's law. The field strength at this nerve site, $|E(\vec{x})|$, is inversely proportional to the squared distance between the nerve site and the electrode, and satisfies Eqn. (1) of EXAMPLE 1.

According to this model, an electrode close to a nerve site requires a relatively small amount of current with a relatively small spread of excitation to activate that site compared to an electrode far from a nerve site. The much larger spread of excitation associated with a distant electrode may result in channel interactions between this electrode and other nearby electrodes that are also distant to nerve sites. It can also be seen that the electric field strength is greatest at an electrode's peak activation region (PAR). Using this model, the activation region (AR) of an electrode is defined as the set of nerve sites that satisfy Eqn. (2) of EXAMPLE 1.

Using this relationship, a nerve site is included in an electrode's AR if the electric field strength at that nerve site exceeds some fraction t of the electric field strength at the PAR, i.e., the ratio of the electric field strength at the nerve site to that at the PAR exceeds some threshold τ. Large values for τ indicate a greater tolerance for overlapping stimulation between electrodes, producing a narrower AR, while small values indicate less tolerance, resulting in a larger AR. In this exemplary study, a default value of τ=0.5 is used, as this value produces similar rates of activation as those reported in studies of the relationship between electrode-to-modiolus distance and the number of effectively independent channels in a CI. Because it is distance-based, this technique can be used to estimate the AR directly from the DVF curves, but there is currently no visual indication of this region on each curve. Thus, identification of the AR is subject to a reviewer's estimation, which may be inconsistently defined across reviewers and across multiple viewings of the curves by the same reviewer over time.

The Activation Region Overlap Image: To overcome the limitations of the DVF curves, a more direct visualization of the AR using the ARO image is disclosed, an example of which is given in FIGS. 6-9. The vertical axis represents each electrode of the array, with each horizontal colored bar associated with one electrode. The most apical electrode is always located at the bottom of the image, and the most basal electrode is always located at the top. The horizontal axis is the same as the log-scale representation of the characteristic frequencies of the ANFs used in the DVF curve visualization. The ARO image uses a similar graphical user interface (GUI) to other 2D visualization approaches for intracochlear electrode location, which show electrode number vs. depth within the cochlea on orthogonal axes, such as that proposed by Ceresa, et al., but with different content, given the use of clinically relevant programming metrics.

This visualization implements Eqn. (2) to define the range of frequencies associated with the nerve sites in the activation region of each electrode. The width of the AR for an electrode is represented by the width of the bar associated with that electrode, as shown in FIGS. 6-9. The PAR of each electrode is indicated using a vertical black line. With this visualization, it is easy to identify when the AR of one electrode overlaps with the PAR of another electrode, an indicator of problematic channel interactions. Additionally, electrodes that either are extracochlear or are intracochlear but very near to the entrance of the cochlea tend to be insufficiently able to stimulate ANFs in a way that improves hearing outcomes and may even cause interference that negatively impacts hearing. Therefore, it is necessitated that, in addition to electrodes that do not satisfy the relationship in Eqn. (2) of EXAMPLE 1, any electrodes with a PAR with characteristic frequency greater than 15 kHz are deactivated.

In addition to explicitly marking the AR and PAR of each electrode, this visualization uses color coding to make violations of the constraints easier to see. The chosen color palette was selected to accommodate users with color blindness. As shown in FIGS. 6-9, electrodes that violate the constraints, i.e., those with too much overlapping stimulation or whose PAR has a place frequency greater than 15 kHz, have bars that are orange in color. When an activated electrode does not violate either of these constraints, the bar for that electrode is green. Deactivated electrodes are indicated with gray bars, unless it could be activated without violating any constraints, in which case its bar is lavender. Finally, the 15 kHz cut-off frequency is indicated with a green line that extends across the entire vertical span of the image.

Figure 7:
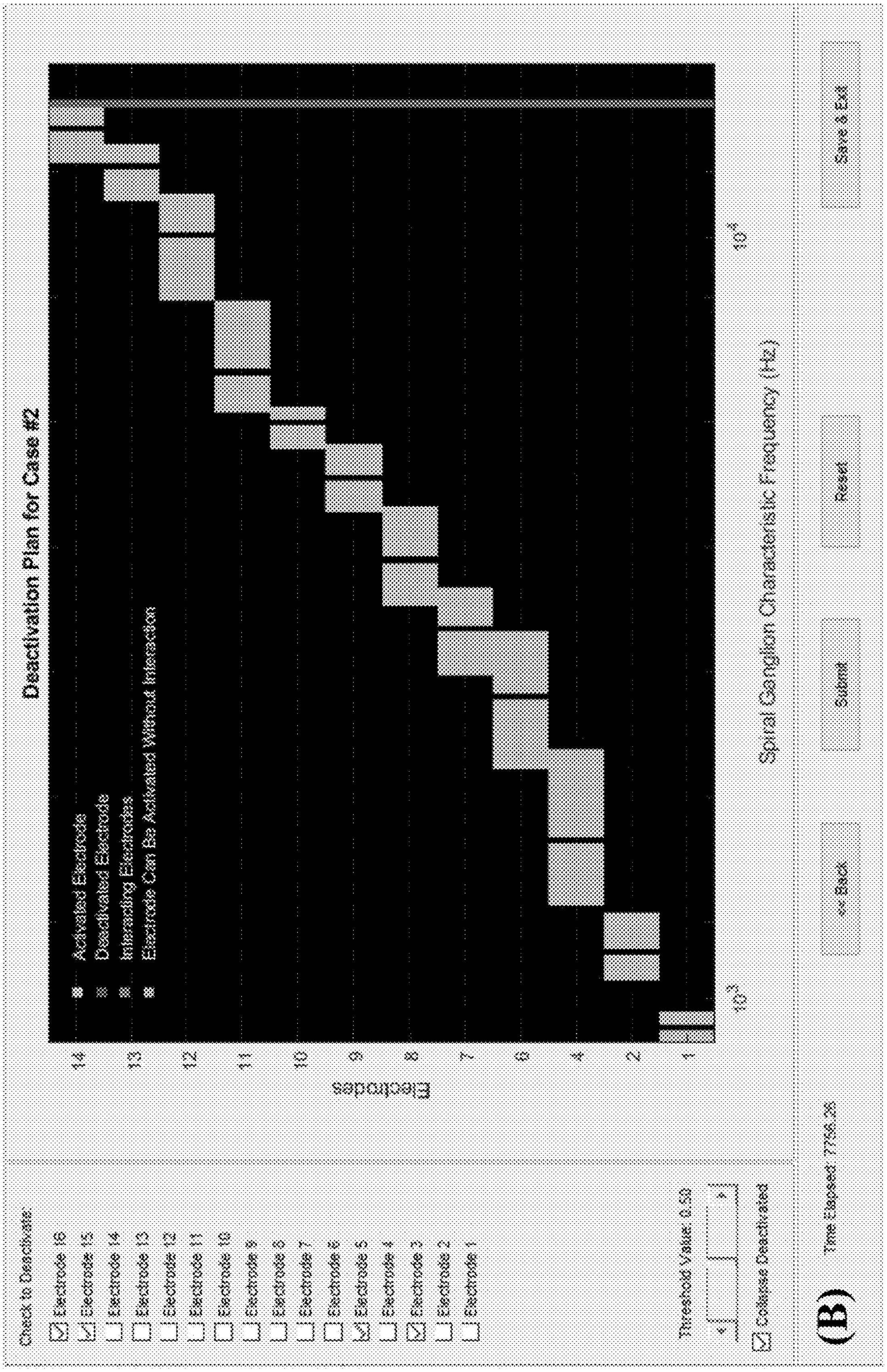
FIG. 7 is an exemplary ARO image, showing a corrected deactivation plan for case No. 2, with no significant interactions.
Figure 8:
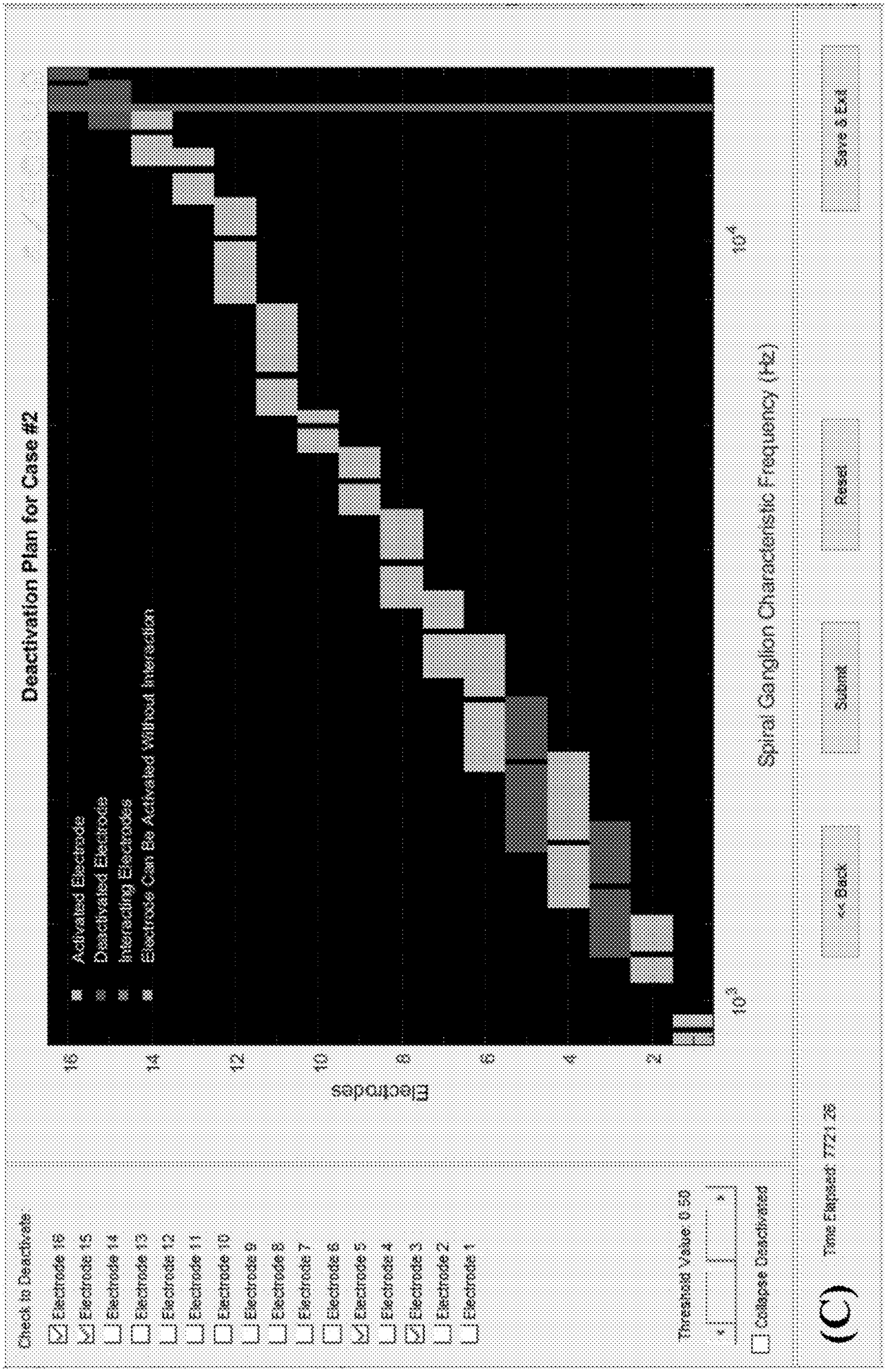
FIG. 8 is an exemplary ARO image, showing only activated electrodes for case No. 2.
Figure 9:
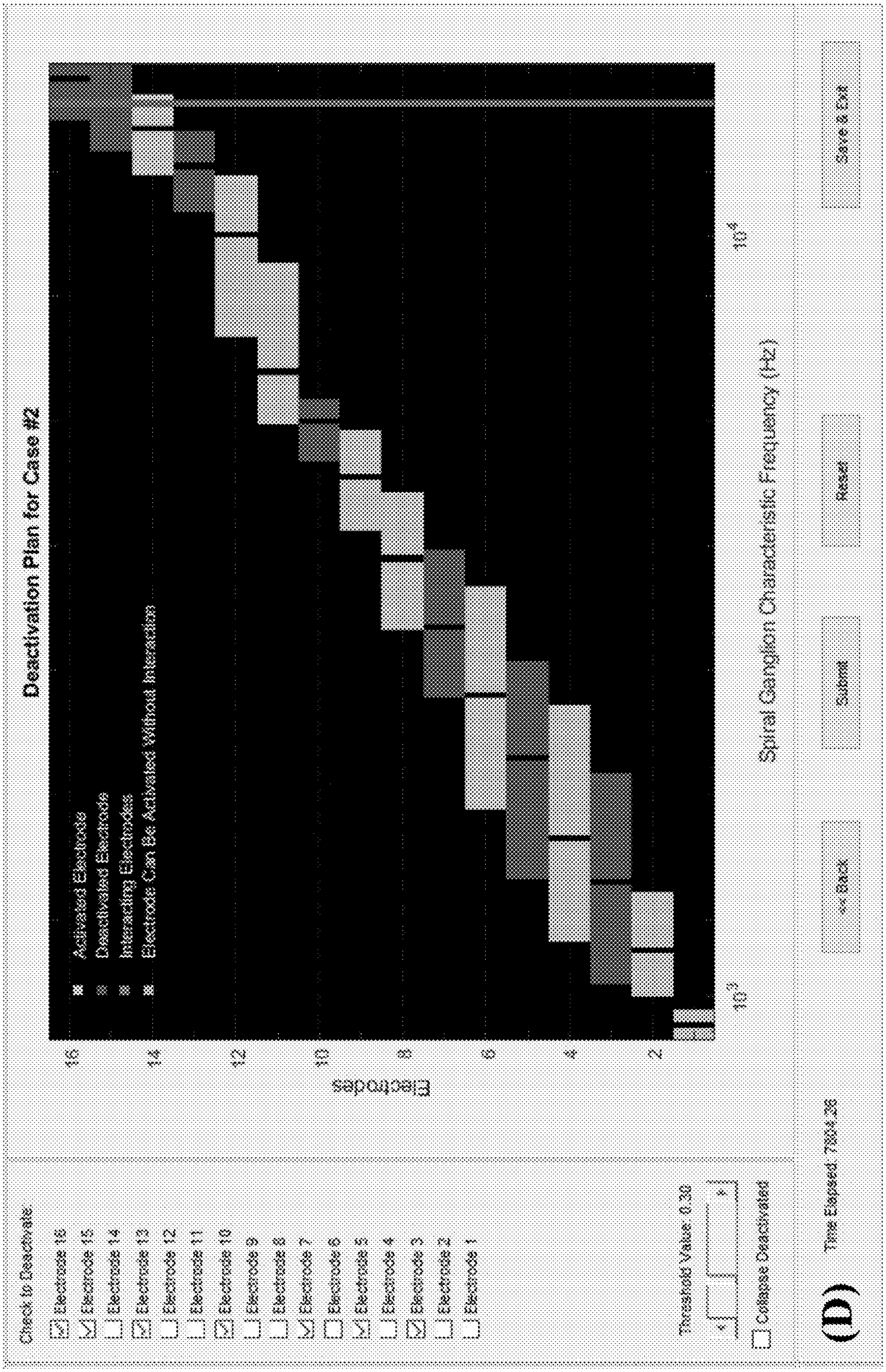
FIG. 9 is an exemplary ARO image, showing the same case (No. 2) from FIGS. 7-8, but with a threshold value of about 0.3.

User Interface: For the purpose of creating new deactivation plans using the ARO image, the visualization is incorporated into an interactive user interface, shown in FIGS. 6-9. Changing any of the available options in the interface automatically triggers the visualization to reassess constraint violations and updated the color for each electrode accordingly. The check boxes to the left of the ARO image control which electrodes are activated or deactivated, where a checked box indicates a deactivated electrode. The user can also modify the threshold value used to determine the AR for each electrode to increase or decrease the tolerance for overlapping stimulation. Finally, if the user wishes to see the frequency range covered by the activated electrodes, they can check the option titled "Collapse Deactivated" at the bottom of the controls on the left to show only activated electrodes, as shown in FIG. 7.

Study Methodology: To evaluate the ARO image against the DVF curves, a multi-part study was designed to determine repeatability of plans generated using each method and optimality of plans generated using each method. In this exemplary study, two reviewers were asked to evaluate each visualization method over 15 cases. Both reviewers were previously familiar with reading DVF curves and received a one-hour training session on using the ARO image.

Experiment 1: Intra-subject variability and time efficiency: In the first part of the exemplary study, reviewers were presented with a set of DVF curves and were asked to generate an electrode deactivation plan for the given case. After all cases were evaluated, the reviewer was asked to repeat this plan generation on the same set of plans, presented in a different random order from the first round. The reviewers then completed a third round of the same evaluation, with the cases once again presented in a different random order. After completing the evaluation of the DVF curves, reviewers repeated this three-round evaluation using the ARO image. Each evaluation was timed to assess the speed with which reviewers developed plans. In this experiment, the reviewer consistency was quantified using the number of plans that differed across each round, the number of differences in those plans, and the time taken to produce plans. The threshold value $\tau$ for each case was also recorded to evaluate the amount of deviation from the default value of 0.5.

Figure 10:
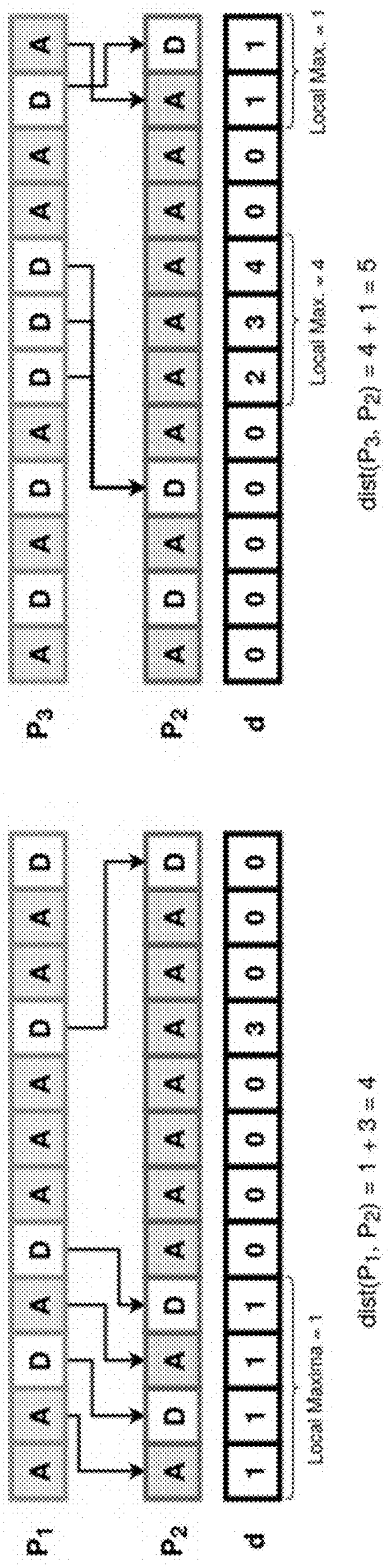
FIG. 10 shows two examples of the modified hamming distance metric detailed in Zhao, et al., (2016) 18. "A" indicates an activated electrode, and "D" indicates a deactivated electrode. Distances are calculated as the difference from plan P1 or P3 to plan P2, where P2 is the same in both examples. Using the MHD metric, P3 is assigned a larger distance than P1 when comparing both to P2.

To measure the number of differences between plans for a single case, a modified version of the Hamming distance, abbreviated as MHD, was use. This modified version penalizes comparisons of certain configuration patterns less harshly compared to the standard Hamming distance. As an example, two plans may both have every other electrode activated, i.e., on-off-on-off, but one plan begins with the first electrode activated while the second has the first deactivated. The standard Hamming distance would be large in this example, despite the plans likely having highly similar stimulation patterns. Instead, the MHD assigns greater values to plans with more distant mismatches in electrode activation status, which likely correspond to plans with greater variations in stimulation patterns. Two examples of calculating the MHD are shown in FIG. 10. When calculating the MHD, if the activation of an electrode k in the first plan does not match that of the corresponding electrode in the second plan, the distance is reported as the number of electrodes between position k and the nearest electrode in the second plan whose activation status matches that of electrode k. This produces an array of distances, from which the local maxima can be identified and summed to get the value for the MHD. To account for the varying number of electrodes in implants, the MHD is then normalized by dividing by the number of electrodes in the array for that case.

Figure 11:
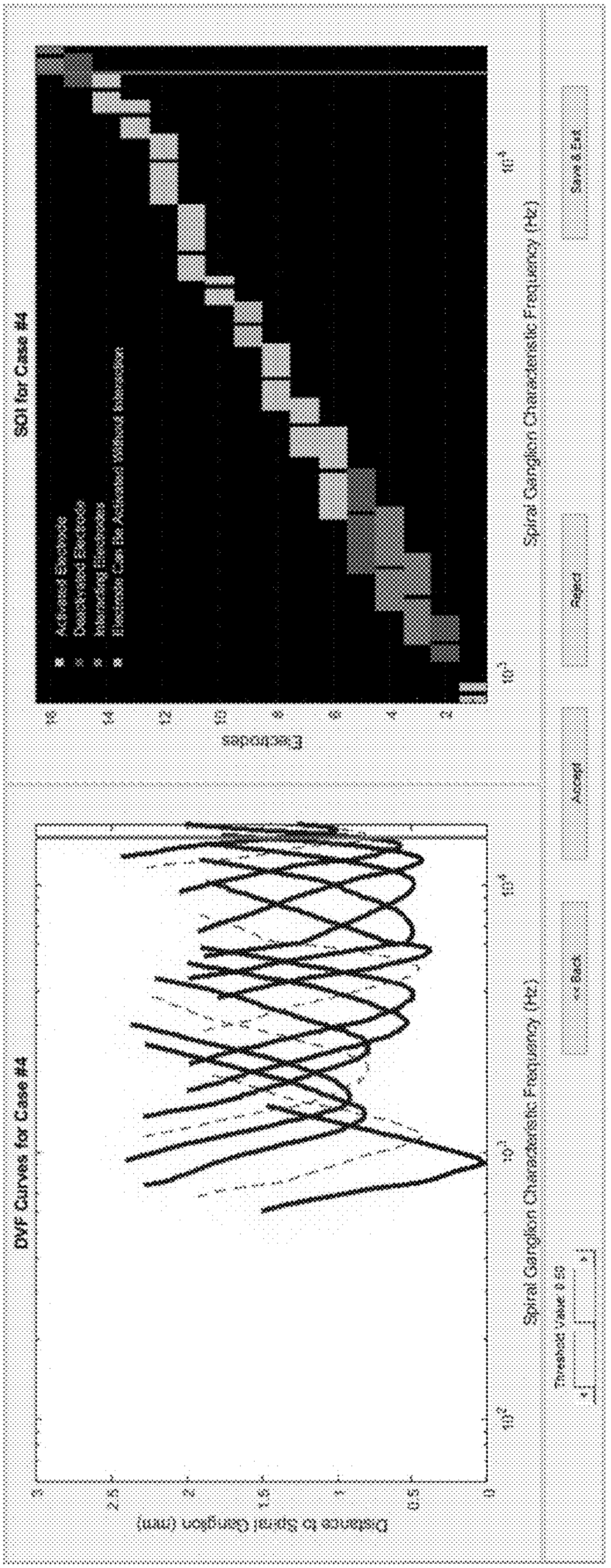
FIG. 11 shows an example of the GUI created for experiment 2, showing one of the randomly selected plans for the same case shown in the previous figures. The same deactivation plan is shown side-by-side on both the DVF curves and the ARO image. The reviewer can manipulate the threshold value to control the tolerance for stimulation overlap.

Experiment 2: Plan optimality: In the second part of the exemplary study, reviewers were asked to judge optimality of plans created during the first part of the exemplary study. For each reviewer, two plans were randomly selected for each case from the set of plans that reviewer created in experiment one: one from their plans created using the DVF curves and one from their plans created using the ARO image. A third plan for each case, a control plan created by another expert that is designed to appear close-to-optimal but is still sub-optimal, was also included. The inclusion of this plan evaluates a reviewer's bias toward accepting all plans. For example, if a reviewer accepts a large number of control plans, that reviewer likely has a bias toward accepting all plans. Again, it should be noted that in this second experiment, the reviewers were evaluating plans for the same cases, but not necessarily the same deactivation plans, as the non-control cases each reviewer evaluated were drawn from those generated by that same reviewer. These cases were presented one at a time in random order to the reviewers, with the origin of the plan masked. For each case, the deactivation plan was shown side-by-side on the DVF curves and ARO image, using the interface shown in FIG. 11. Reviewers evaluated if the plan was optimal or not, i.e., a plan should only be accepted if the reviewer would not change anything about it. The reviewer did have the option to adjust the threshold value for individual plans if they felt the default value of 0.5 had either too much or too little tolerance for overlap, based solely on the information provided in the visualizations.

Results

A summary of the results from the first experiment for the DVF curves and the ARO image is shown in Table 2. The number of differences between plans for a single case is reported in terms of the normalized MHD introduced in the previous section. From these preliminary results, it is shown that plan selection using the ARO image is more consistent across cases, and when differences do occur, the number of differences between two plans is lower compared to the DVF curves. Additionally, the average time taken to generate a plan is lower for the ARO image than that for the DVF curves. Two-sided Wilcoxon rank sum tests indicated the differences in the time taken to generate a plan and the consistency of the plans created for a case when using the DVF curves versus the ARO image were both highly statistically significant ($p<10^{-15}$ and $p<10^{-12}$, respectively). It is found that an average value of $\tau=0.534$ across both reviewers.

TABLE 2

A summary of the results for the generation of plans using DVF curves and the ARO image in part 1 of the study.

| | Reviewer | # of Varied Plans | Mean Normalized MHD | Median Time (s) |
|---|---|---|---|---|
| DVF | 1 | 29 | 0.156 | 99 |
| | 2 | 21 | 0.170 | 51 |
| ARO | 1 | 3 | 0.009 | 31 |
| | 2 | 6 | 0.0133 | 17 |

The second part of the study was evaluated on the total number of plans from each method rated as optimal. A summary of these results is given in Table 3. It is shown that ARO image plans are rated as optimal at a greater rate than DVF curve plans, with an acceptance rate of 93.3% and 66.7%, respectively. The acceptance of zero control plans by both reviewers indicates a low likelihood of bias toward accepting all plans. Again used the Wilcoxon rank sum test was used to assess the accuracy of each method of plan generation versus the others. It is found that the difference in acceptance rates for the plans created using DVF curves and the plans created using ARO images was statistically significant ($p<10^{-5}$). The differences in acceptance rates for both the DVF curves and the ARO images compared to acceptance rates for the control plans were also statistically significant, with $p=0.02$ and $p=3.8\times10^{-10}$, respectively.

TABLE 3

A summary of the results for the evaluation of plans generated by each method in part 2 of the study.

| Reviewer | DVF Plans Accepted | ARO Plans Accepted | Control Plans Accepted |
|---|---|---|---|
| 1 | 1 | 10 | 0 |
| 2 | 4 | 14 | 0 |

Conclusion

Briefly, the exemplary study discloses, among other things, a visualization method that utilizes patient-specific spatial information of intracochlear anatomy and electrode array positioning to determine the AR of an electrode using electric field strength estimates and displays this information in an easy-to-read format. This visualization removes the need to mentally estimate the AR and PAR of each electrode required when using DVF curves, decreasing subjectivity of plan generation. These results indicate that the ARO image outperforms the DVF curves in repeatability, acceptability, and time taken to generate plans. In a separate study, automatic methods for selecting deactivation plans were also evaluated. The use of this visualization technique to review automatic plans will be evaluated in the future. This visualization method is also used to explore the effectiveness of the default threshold value of $\tau=0.5$ for generating deactivation plans that result in improved hearing assessment scores.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the invention pertains without departing from its spirit and scope. Accordingly, the scope of the invention is defined by the appended claims rather than the foregoing description and the exemplary embodiments described therein.

Some references, which may include patents, patent applications and various publications, are cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

LIST OF REFERENCES

[1] NIDCD Quick Statistics About Hearing, https://www.nidcd.nih.gov/health/statistics/quick-statistics-hearing, last accessed 2020 Mar. 13.

[2] NIDCD Fact Sheet: Cochlear Implants. National Institute on Deafness and Other Communication Disorders. NIH Publication No. 11-4798. https://www.nidcd.nih-.gov/sites/de-fault/files/Documents/health/hearing/FactSheetCochlearImplant.pdf, last accessed 2020 Mar. 12.

[3] Holden, L., Finley, C., Firszt, J., et al.: Factors affecting open-set word recognition in adults with cochlear implants. Ear Hear 34, 342-360 (2013).

[4] Finley, C., Skinner, M.: Role of electrode placement as a contributor to variability in cochlear implant outcomes. Otol Neurotol 29, 920-928 (2008).

[5] Chakravorti, S., Noble, J., Gifford, R., Dawant, B., O'Connell, B., Wang, J., Labadie, R.: Further evidence of the relationship between cochlear implant electrode positioning and hearing outcomes. Otology & Neurotology 40 (5), 617-624 (2019).

[6] Aschendorff, A., et al: Quality control after cochlear implant surgery by means of rotational tomography. Otology & Neurotology 26 (1), 34-37 (2005).

[7] Wanna, G., et al: Impact of electrode design and surgical approach on scalar location and cochlear implant outcomes. Laryngoscope 124 (6), S1-S7 (2014).

[8] Wanna, G., et al: Assessment of electrode placement and audiologic outcomes in bilateral cochlear implantation. Otology & Neurotology 32 (3), 428-432 (2011).

[9] O'Connell B. P., et al: Electrode location and angular insertion depth are predictors of audiologic outcomes in cochlear implantation. Otology & Neurotology 37 (8), 1016-1023 (2016).

[10] Noble, J. H., Labadie, R. F., Gifford, R. H., and Dawant, B. M.: Image-guidance enables new methods for customizing cochlear implant stimulation strategies. IEEE Trans. on Neur. Sys. and Rehab. Eng. 21 (5), 820-829 (2013).

[11] Noble, J. H., Gifford, R. H., Labadie, R. F., and Dawant, B. M.: Statistical shape model segmentation and frequency mapping of cochlear implant stimulation targets in CT. Proc. MICCAI 2012 LNCS Vol. 15 (2), 421-428 (2012).

[12] Zhao, Y., et al.: Automatic graph-based method for localization of cochlear implant electrode arrays in clinical CT with sub-voxel accuracy. Med. Image Anal. 52, 1-12 (2019).

[13] Noble, J. H., Dawant, B. M.: Automatic graph-based localization of cochlear implant electrodes in CT. In: Navab, N., Hornegger, J., Wells, W. M., Frangi, A. F. (eds.) MICCAI 2015. LNCS, vol. 9350, pp. 152-159. Springer, Cham (2015). https://doi.org/10.1007/978-3-319-24571-3_19.

[14] Baer, T. and Moore, B. C. J.: Effects of spectral smearing on the intelligibility of sentences in the presence of interfering speech. J. Acoust. Soc. Am. 95, 2277-2280 (1994).

[15] Kwon, B. J.: Effects of electrode separation between speech and noise signals on consonant identification in cochlear implants. J. Acoust. Soc. Am. 126 (6): 3258-67 (2009). https://doi.org/10.1121/1.3257200.

[16] Berg, K. A., Noble, J. H., Dawant, B. M., Dwyer, R. T., Labadie, R. F., Gifford, R. H.: Speech recognition as a function of the number of channels for an array with large inter-electrode distances. J. Acoust. Soc. Am. 149 (4): 2752-63 (2021).

[17] Rattay, F., Leao, R. N., and Felix, H.: A model of the electrically excited human cochlear neuron. II. Influence of the three-dimensional cochlear structure on neural excitability. Hear Res 153 (1-2), 64-79 (2001).

[18] Ceresa, M., Lopez, N. M., Velardo, H. D., Herrezuelo, N. C., Mistrik, P., Kjer, H. M., Vera, S., Paulsen, R. R., and Ballester, M. A. G.: Patient-specific simulation of implant placement and function for cochlear implantation surgery planning. Proc. MICCAI 2014 LNCS Vol. 8674, 49-56 (2014).

[19] Zhao, Y., Dawant, B. M., and Noble, J. H.: Automatic selection of the active electrode set for image-guided cochlear implant programming. Journal of Medical Imaging Vol. 3 (3), 035001 (2016).

[20] Bratu, E. L., Dwyer, R., and Noble, J. H.: A graph-based method for optimal active electrode selection in cochlear implants. Proc. MICCAI 2020 LNCS Vol. 12263, 34-43 (2020).

[21] Zhang, D., Zhao, Y., Noble, J. H., Dawant, B. M: Selecting electrode configurations for image-guided cochlear implant programming using template matching. Journal of Medical Imaging, Vol. 5 (2), 021202 (2018).

What is claimed is:

1. A method for active electrode selection in a cochlear implant having an electrode array with a plurality of electrodes implanted in a cochlea of a living subject, comprising:

estimating, by a computing device using patient-specific anatomical data derived from medical imaging, an activation region (AR) of each electrode based on its distance to nerve sites;

automatically finding, by execution of a graph-based optimization algorithm on the computing device, a set of active electrodes that do not have AR overlap, wherein the graph-based optimization algorithm comprises:

defining a graph having a set of nodes, $N=\{n_i\}$, and edges, $E=\{e_{ij}\}$, wherein each node, $n_i$, represents an electrode in the electrode array, and edge $e_{ij}$ is a directed edge connecting electrode i to electrode/ with cost; and determining an optimal path traversing edges connecting nodes with a minimum cumulative edge cost in the graph, wherein the nodes in the optimal path are corresponding to an optimal set of active electrodes; and electrically stimulating auditory nerve fibers by activating electrodes in the optimal set and deactivating electrodes not in the optimal set, thereby reducing channel interaction and improving auditory signal resolution.

2. The method of claim 1, wherein the nodes in the optimal path include a starting node and an ending node, wherein the starting node for the path is selected to be the most apical contact, and wherein the ending node for the path is selected to be the electrode with PAR among the highest frequency nerves that can be effectively stimulated near the basal end of the cochlea.

3. The method of claim 2, wherein the ending node for the path is selected by defining a decision plane based on the one-to-one point correspondence between the segmentation in the patient image and an atlas image, wherein the decision plane is located where nerves with characteristic frequencies of about 15 kHz are located; and selecting the first electrode that lies apically to the decision plane as the ending node of the path.

4. The method of claim 2, wherein the edges E are defined to permit finding the optimal path with the minimum cumulative edge cost from the starting node to the ending node that represents the optimal set of active electrodes.

5. The method of claim 4, wherein hard constraints for edge $e_{ij}$ to exist and soft constraints for edge costs defined by a cost function $C(e_{ij})$ are used to ensure the minimal path corresponds to the optimal set of active electrodes.

6. The method of claim 5, wherein edge $e_{ij}$ exists only when first and second conditions are satisfied, wherein the first condition is i<j, which ensures the path traverses from the most apical electrode to a sequence of increasingly more basal neighbors until reaching the ending node, and the second condition is the AR for electrode j does not include the PAR for electrode i and vice versa.

7. The method of claim 6, wherein the AR of the electrode is a group of nerve sites that satisfy:

$$R = \frac{|E(\vec{x})|}{|E(PAR)|} = \frac{\|PAR - \vec{c}\|^2}{\|\vec{x} - \vec{c}\|^2} > \tau$$

wherein $|E(\vec{x})|$ and $|E(PAR)|$ are electric field strengths from the electrode $\vec{c}$ at a nerve site $\vec{x}$ of the group of nerve sites and its peak activation region (PAR), respectively, R is a ratio of the electric field strength from the electrode at the nerve site to that at the PAR, and $\tau$ is a threshold value to determine the AR for the electrode.

8. The method of claim 5, wherein the soft constraints are encoded in the cost function $C(e_{ij})$ that satisfies, $$C(e_{ij}) = \alpha d_i + (1-\alpha)\beta^{(j-i-1)}$$

wherein $d_i = \|PAR_i - \vec{c}_i\|$ is the distance from electrode i to its PAR, and $\alpha$ and $\beta$ are parameters with $0<\alpha<1$ and $\beta>1$, wherein the first term in the cost function rewards active electrodes that tend to have shorter distance to SG sites; and wherein the second term in the cost function is used to ensure as many electrodes are active as allowable by the hard constraints, wherein when j=i+1, no electrodes are deactivated, when j>i+1, some electrodes are skipped in the path, which are to be deactivated; and when j>>i+1, a larger cost is assigned when deactivating multiple electrodes in sequence to discourage deactivations that result in large gaps in neural sites where little stimulation occurs.

9. The method of claim 8, wherein Djikstra's shortest-path algorithm is used to determine a global cost minimizing path in the graph, wherein the resulting path represents the set of electrodes that remains active, while electrodes not in the path is recommended for deactivation.

10. A system for active electrode selection, comprising:

a CI device being implanted in a cochlea of a living subject, the CI device comprising an electrode array having a plurality of electrodes; and at least one computing device having one or more processors and a storage device storing computer executable code, wherein the computer executable code, when executed at the one or more processors, is configured to perform the method of claim 1 for active electrode selection in the CI device.

11. A non-transitory computer-readable medium storing computer executable code, wherein the computer executable code, when executed at one or more processors, causes a system to perform the method of claim 1 for active electrode selection in a cochlear implant having an electrode array with a plurality of electrodes implanted in a cochlea of a living subject.

* * * * *